US008961427B2

(12) United States Patent
Owsley et al.

(10) Patent No.: US 8,961,427 B2
(45) Date of Patent: *Feb. 24, 2015

(54) SPECTRUM ANALYSIS OF CORONARY ARTERY TURBULENT BLOOD FLOW

(71) Applicant: Phonoflow Medical, LLC, Gales Ferry, CT (US)

(72) Inventors: Norman Lee Owsley, Gales Ferry, CT (US); Roger Paul Norris, Viera, FL (US); Ralph Walter Zaorski, Davenport, FL (US)

(73) Assignee: Phonoflow Medical, LLC, Gales Ferry, CT (US)

( * ) Notice: Subject to any disclaimer, the term of this patent is extended or adjusted under 35 U.S.C. 154(b) by 45 days.

This patent is subject to a terminal disclaimer.

(21) Appl. No.: 13/815,961

(22) Filed: Mar. 18, 2013

(65) Prior Publication Data

US 2014/0187971 A1  Jul. 3, 2014

Related U.S. Application Data

(63) Continuation-in-part of application No. 12/228,058, filed on Aug. 9, 2008, now Pat. No. 8,419,651.

(51) Int. Cl.
*A61B 5/02* (2006.01)
*A61B 8/06* (2006.01)
*A61B 7/00* (2006.01)
*A61B 5/026* (2006.01)
*A61B 5/00* (2006.01)

(52) U.S. Cl.
CPC ............... *A61B 5/02007* (2013.01); *A61B 7/00* (2013.01); *A61B 5/026* (2013.01); *A61B 5/7257* (2013.01); *A61B 5/7203* (2013.01); *A61B 5/7246* (2013.01); *A61B 2562/0204* (2013.01)
USPC ........................... 600/528; 600/437; 600/454

(58) Field of Classification Search
USPC .......................................... 600/528, 454, 437
See application file for complete search history.

(56) References Cited

U.S. PATENT DOCUMENTS 8,419,651 B2 * 4/2013 Owsley et al. ................ 600/528

* cited by examiner

*Primary Examiner* — Carl H Layno
*Assistant Examiner* — Jon Eric C Morales
(74) *Attorney, Agent, or Firm* — Peloquin, PLLC; Mark S. Peloquin, Esq.

(57) ABSTRACT

Methods and apparatuses are described to obtain cardiac data, which includes acquiring vibrational field cardiac data from a transducer wherein the transducer measures vibration over a surface of a human's body. An unwanted coronary event is separated from vibrational cardiac data. A transient event is extracted from the vibrational cardiac heart cycle data. The transient event occurs during a diastolic interval within a heart cycle. The transient event is evaluated for a condition of coronary artery blood flow turbulence and a condition of health of a coronary artery is assessed from a feature in the vibrational frequency power spectrum estimate.

118 Claims, 28 Drawing Sheets

US 8,961,427 B2

SPECTRUM ANALYSIS OF CORONARY ARTERY TURBULENT BLOOD FLOW

RELATED APPLICATIONS

This application is a continuation-in-part of U.S. patent application Ser. No. 12/228,058 filed on Aug. 9, 2008, which is now U.S. Pat. No. 8,419,651.

BACKGROUND OF THE INVENTION

1. Field of Invention

The invention relates generally to detecting and processing vibrational cardiac data, and more specifically to apparatuses and methods used to detect vibrational cardiac data related to coronary artery disease.

2. Art Background

Coronary artery disease is a primary precursor of heart attacks, which is a leading cause of death in the United States. Coronary artery disease is characterized by a deposition of plaque within the coronary arteries, resulting in a condition referred to as stenosis, in which case blood flow is restricted and the oxygen supply to the heart muscle is decreased. Such a deposition of plaque is also referred to as an occlusion. Coronary artery disease can result in heart attack and subsequent physical injury and possible death. This can present a problem.

It is known that the blood flow can become turbulent as the blood passes through an area of stenosis. Turbulent blood flow provides a source of vibrational excitation within the body. The vibrational excitation causes energy to propagate through the body and provides a field that can be measured at the surface of the body. Normal body functions such as breathing and the opening and closing of the heart's valves provide high levels of background noise relative to the magnitude of the vibrational energy resulting from excitation at areas of stenosis. Such high levels of background noise can frustrate detection. This can present a problem.

The body is made up of structures that have very different physical properties which are distributed as a function of space throughout the body cavity. Some of these structures are lungs, ribs, organs, blood, arteries, fat, etc. These structures present a non-homogeneous media to the propagation of vibrational energy. Such a non-homogenous media can make it difficult to characterize the media sufficiently to form focused listening beams while processing the vibrational energy emitted from the areas of stenosis during a parametric analysis that assumes a known vibrational wave speed. This can present a problem.

Currently, coronary artery disease is treated post symptomatically with an invasive procedure called an angiogram. The angiogram is costly, invasive, and places the patient at risk of injury due to complications that can arise during the procedure. All of this can present problems.

BRIEF DESCRIPTION OF THE DRAWINGS

The invention may best be understood by referring to the following description and accompanying drawings that are used to illustrate embodiments of the invention. The invention is illustrated by way of example in the embodiments and is not limited in the figures of the accompanying drawings, in which like references indicate similar elements.

22, rendered in part with a grey scale image according to embodiments of the invention.

Figure 22:
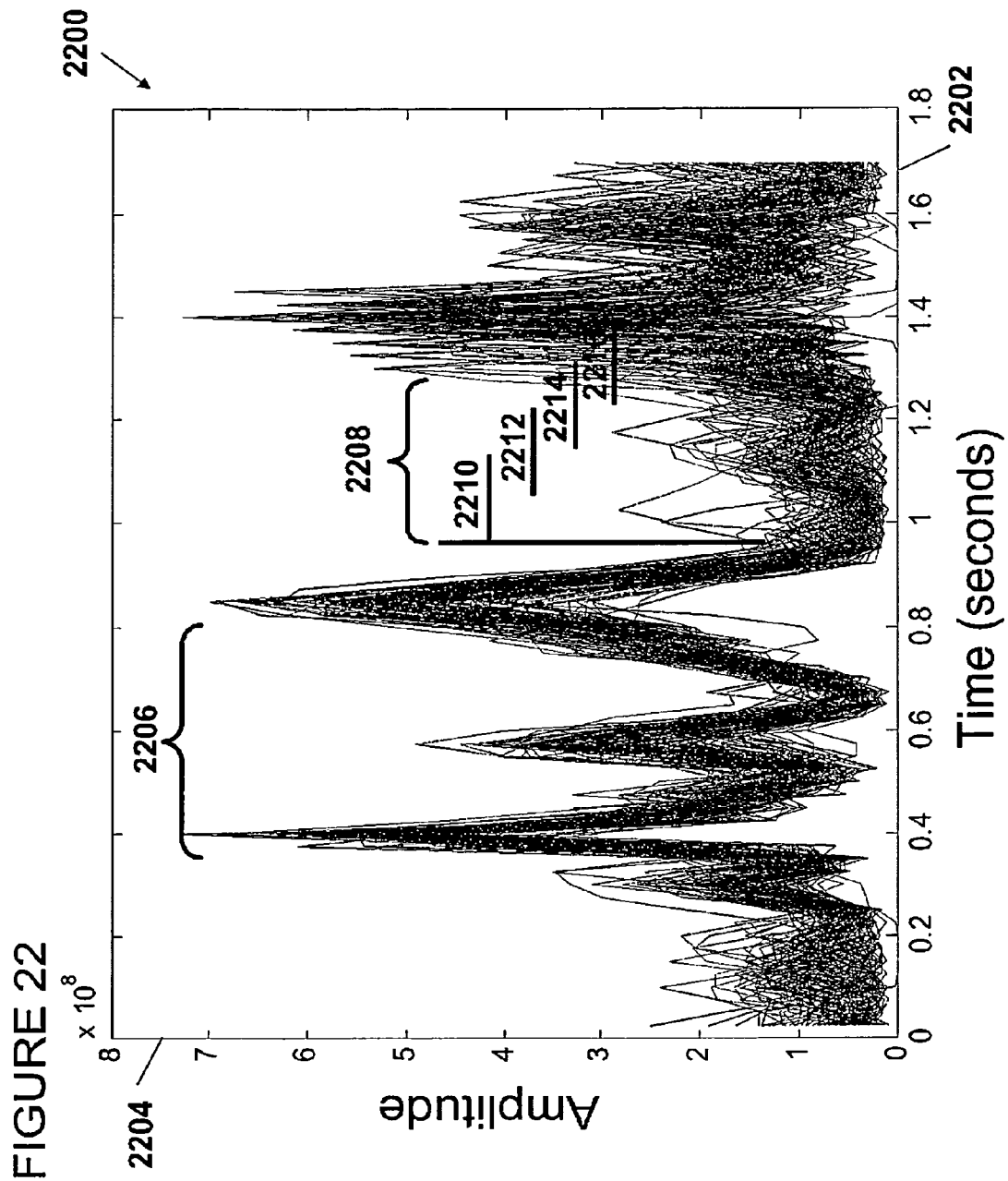
FIG. 22 illustrates a set of time series plots of vibrational cardiac data collected from a human with coronary artery disease, according to embodiments of the invention.
Figure 24:
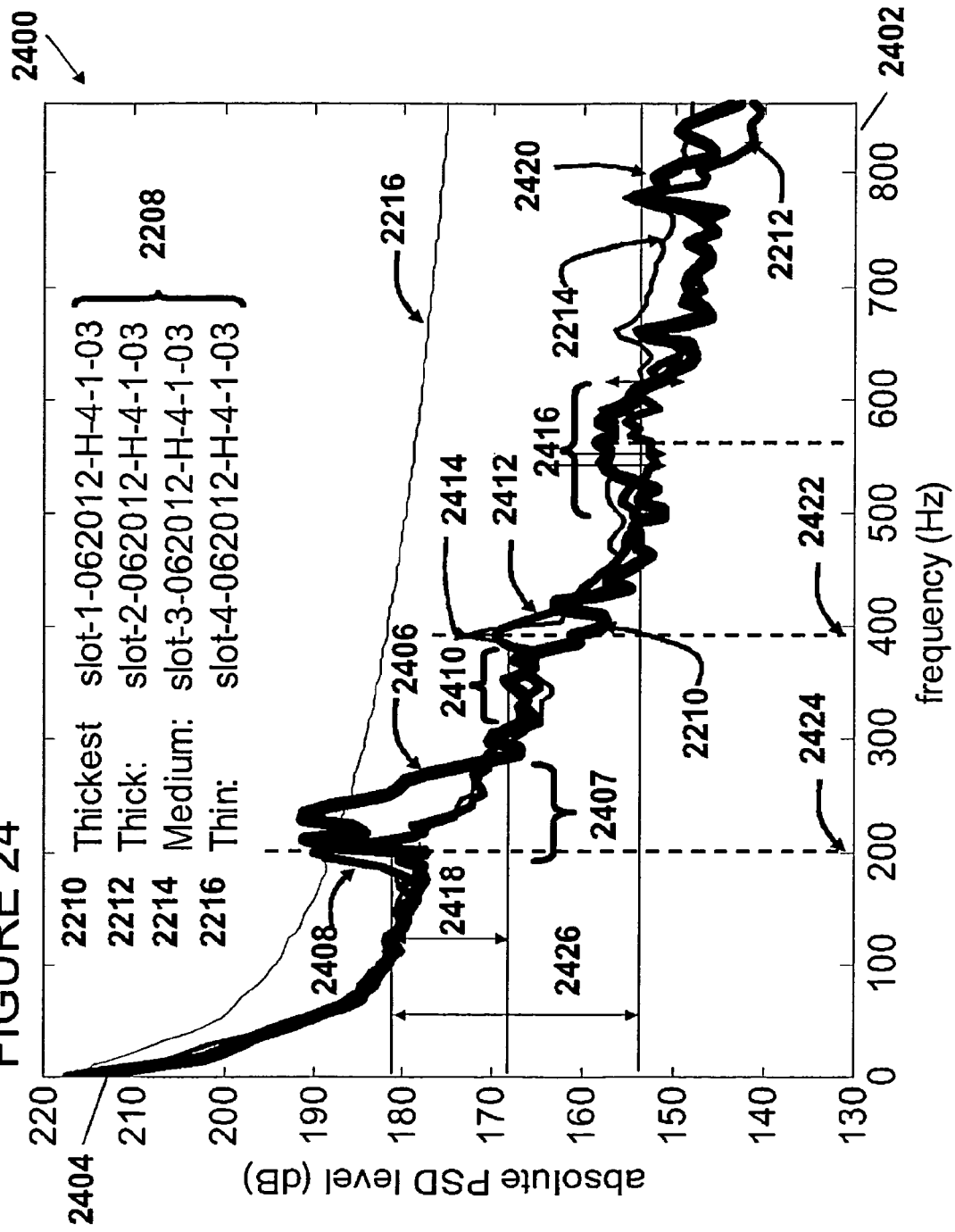

FIG. 24 illustrates an overlay of vibrational frequency power spectra estimates from multiple slots corresponding to the human's data shown in FIG. 22, according to embodiments of the invention.

Figure 25:
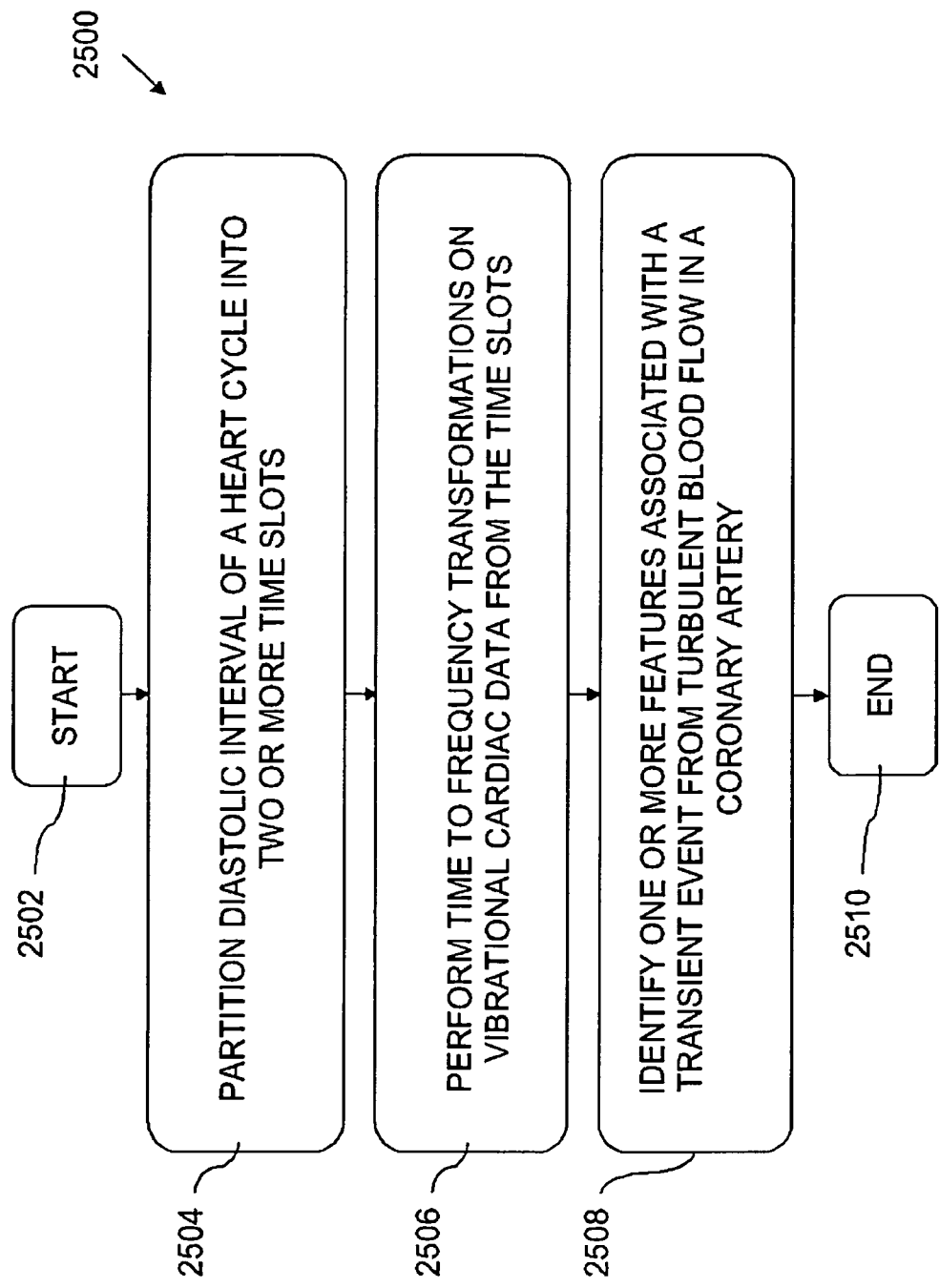

FIG. 25 illustrates a method for identifying a feature related to coronary artery blood flow turbulence using a single human, according to embodiments of the invention.

Figure 26:
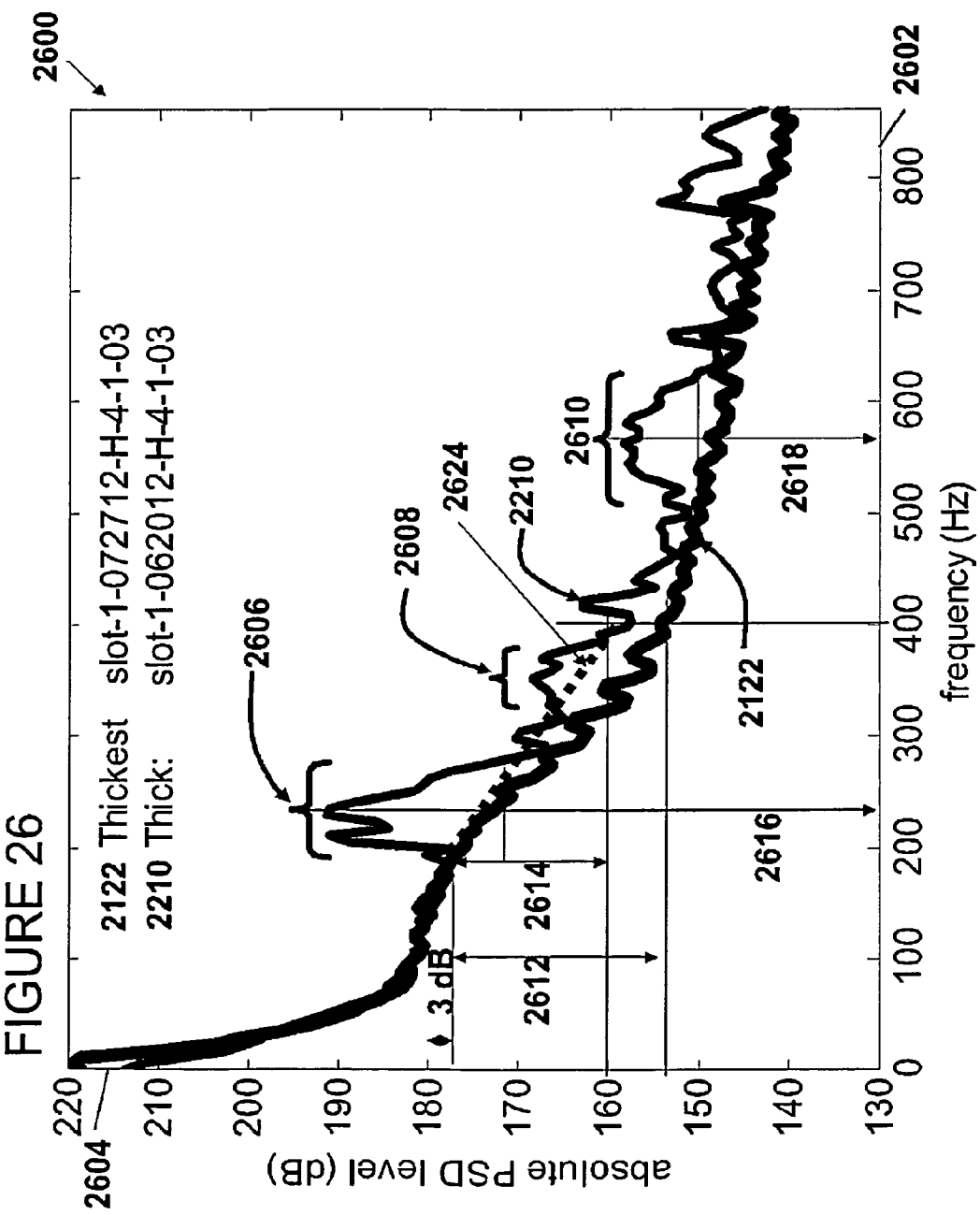

FIG. 26 illustrates a comparison of vibrational cardiac data from multiple humans, according to embodiments of the invention.

Figure 27:
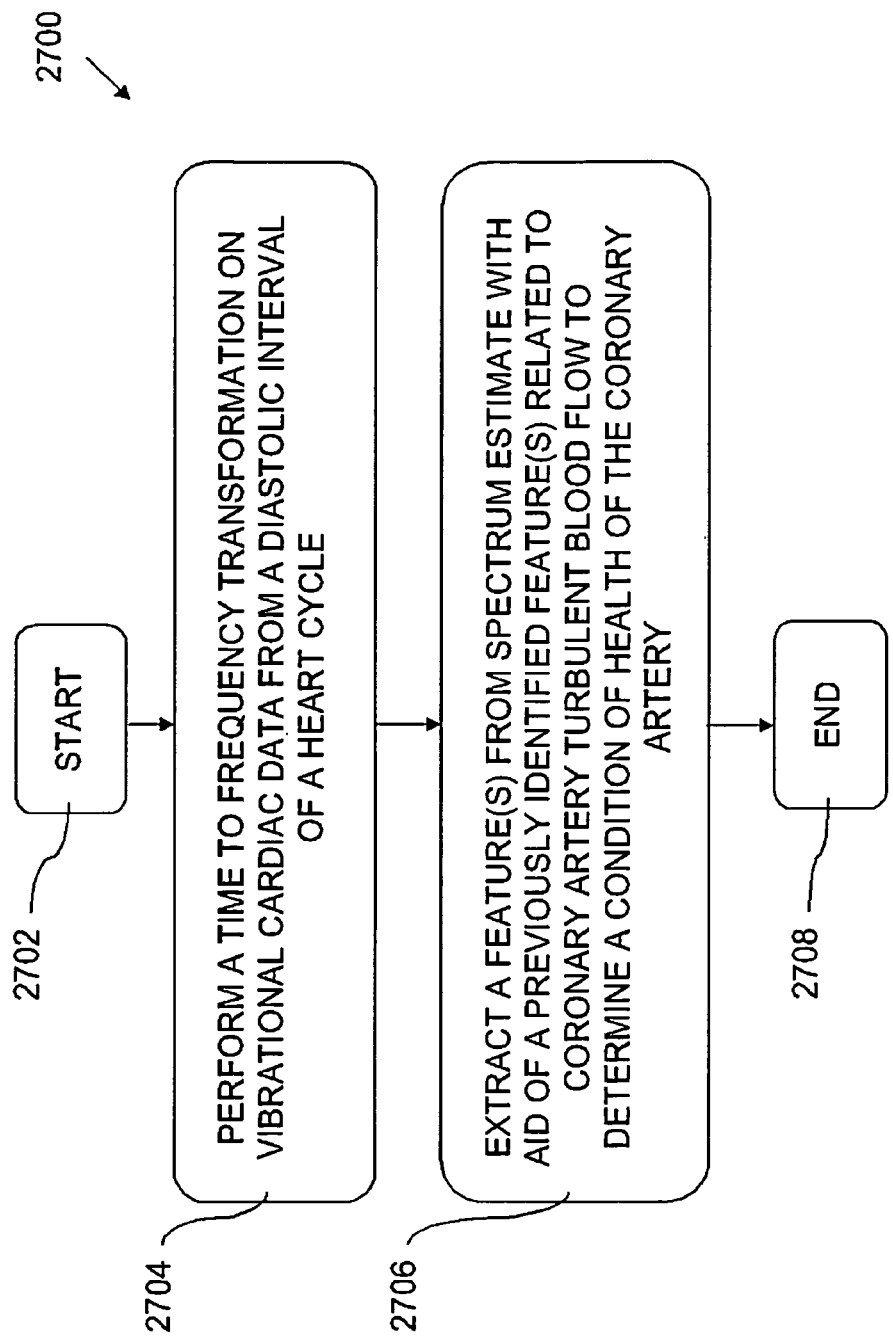

FIG. 27 illustrates a method for identifying a feature related to coronary artery blood flow turbulence using multiple humans, according to embodiments of the invention.

DETAILED DESCRIPTION

In the following detailed description of embodiments of the invention, reference is made to the accompanying drawings in which like references indicate similar elements, and in which is shown by way of illustration, specific embodiments in which the invention may be practiced. These embodiments are described in sufficient detail to enable those of skill in the art to practice the invention. In other instances, well-known circuits, structures, and techniques have not been shown in detail in order not to obscure the understanding of this description. The following detailed description is, therefore, not to be taken in a limiting sense, and the scope of the invention is defined only by the appended claims.

Apparatuses and methods are described for detecting and processing vibrational cardiac data in a human. In one or more embodiments, the vibrational cardiac data arises from stenosis in a coronary artery. In one embodiment, vibrational cardiac data is measured and processed from a phantom with and without stenosis.

Figure 1A:
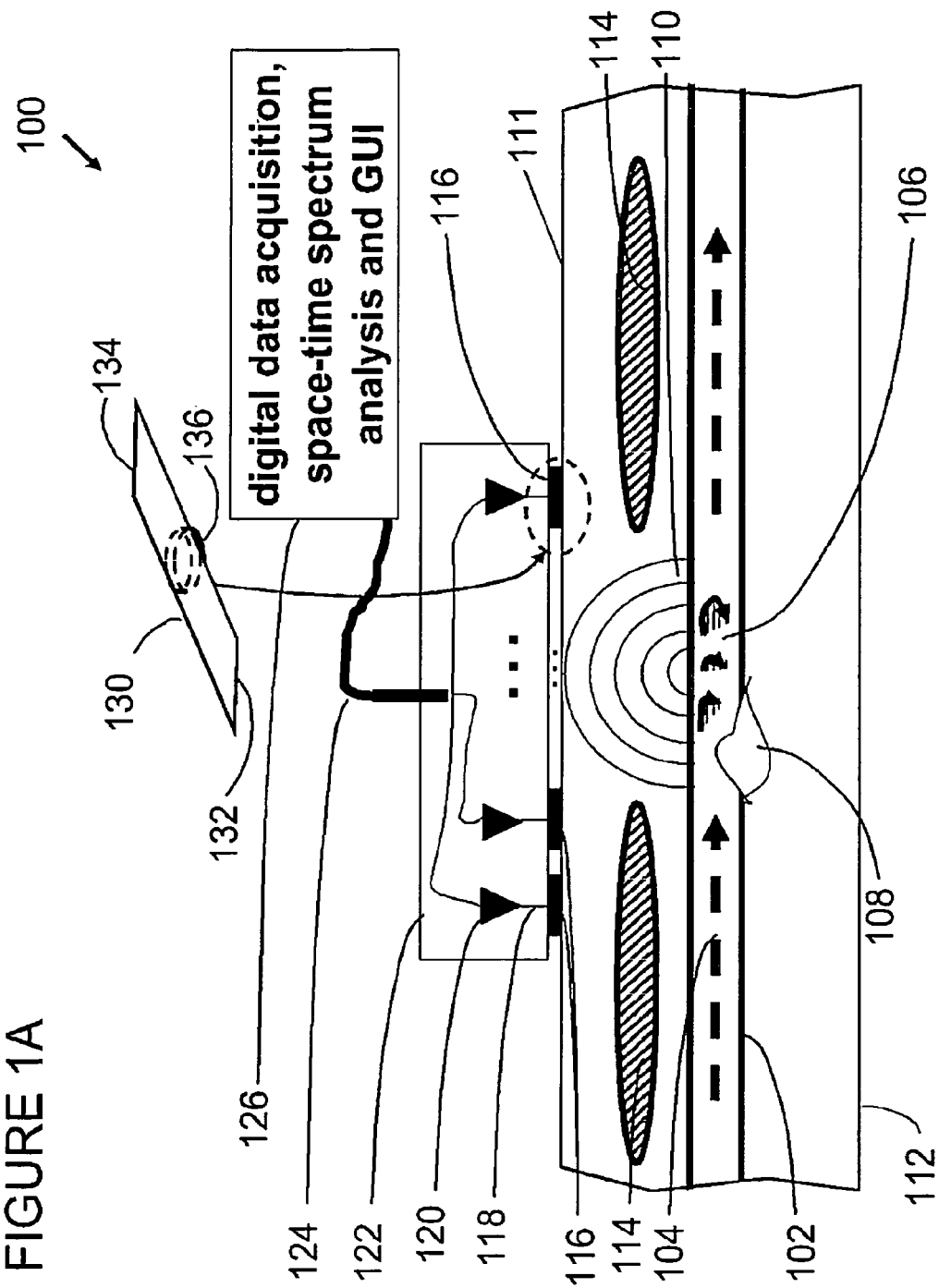
FIG. 1A illustrates an apparatus, according to one embodiment of the invention.

FIG. 1A illustrates an apparatus generally at 100, according to one embodiment of the invention. With reference to FIG. 1A, a cross-section 112 of a human body contains coronary artery 102 having a flow of blood 104 passing therethrough. The flow of blood 104 can interact with a coronary artery lesion 108 and cause an excitation of the artery wall by known physical means, which include transition to turbulent flow 106 and the corresponding application of forces normal to the surface of the coronary artery. Such excitation of the coronary artery wall results in vibrational energy 110 propagating to the surface of the human 111.

In this description of embodiments, the term "sensor" is synonymous with the terms "channel" or "sensor channel," whereby a separate measurement is contemplated. Additionally, the term "sensor" is synonymous with the terms "transducer" or "sensing transducer." Thus, a first sensor's output (a first channel) and a second sensor's output (a second channel) are each available for analysis and each represents a separate measurement of a field quantity of interest, such as the vibration field in a human's body. As will be noted by those of skill in the art, in some instances, it might be advantageous to electrically combine together, in series or parallel, several sensors into a single channel. Such combinations can be made within the scope of the descriptions provided herein. However to simplify the discussion, "sensor" will be understood to be synonymous with the terms "sensor channel," "channel," "transducer," or "sensing transducer."

An array of sensors 116 measures the vibration of the surface 111 and collects vibrational cardiac data thereby. The array of sensors 116 is made up of a general number of N sensors (sensing transducers or transducers). In one embodiment, the number N equals 14 and the spacing between adjacent transducers is one-quarter inch (0.25"). Those of skill in the art will recognize that the array of N sensors 116 can be configured with; a different number of sensors, a different sensor width, and/or sensor spacing. The example given herein is provided merely for illustration and does not limit embodiments of the invention.

The cross section 112 of the human presents a non-homogeneous media through which the vibrational energy 110 propagates and contains various structures such as ribs, lungs, organs interfaces, muscles, fat, and skin tissue indicated generally by 114. The vibrational energy propagates through the non-homogeneous media and is measured on the surface 111 by the array of N sensors 116. In one embodiment, it can be desirable to place the array of sensors 116 over a person's heart and above a space between adjacent ribs to facilitate detection of the vibrational energy.

In one embodiment, each sensor of the array of sensors 116 is made from a strip of polyvinylidene fluoride (PVDF) film. In one example, each strip of PVDF film measures 0.75 inches long, between attachments to a chassis 122, and 0.1875 inches wide. Each strip of PVDF film is stretched into a flat plane and is anchored at each end by the chassis 122. At the midpoint of each strip of PVDF film, a pad is placed to provide an area of contact between the skin surface 111 and the strip of PVDF film. An example of one such sensor from the array of sensors 116 is illustrated by a strip of PVDF film 130, having a first end 132 and a second end 134 (which are attached to the chassis 122) and a pad 136 that makes contact with the skin surface 111. In one embodiment, the diameter of the pads is 0.1875 inches and the thickness of the pads is 0.0625 inches. The sensitivity of the PVDF film along its major axis is 22176 V/unit strain for a PVDF film thickness of 0.028 millimeters. The PVDF film generates a voltage in response to strain imparted from the motion of the skin surface 111. In one embodiment, the chassis 122 is made out of metal such as aluminum, in other embodiments the chassis 122 is made out of plastic or another material sufficient to provide the necessary anchor points for the strips of PVDF film.

Each sensing transducer is in electrical contact with at least one preamplifier 120 using connection 118. It is advantageous to place a preamplifier proximate to its sensing transducer in order to minimize the addition of electronic noise. Additional amplification stages can be used and in one embodiment the outputs from the preamplifiers 120 are passed to a bank of amplifiers (not shown), such as those available from Ithaco Corporation Model 451. In one embodiment, the outputs of the sensing transducers (array 116) are carried in a cable bundle 124 and are processed in a data acquisition system 126 that can contain a graphical user interface (GUI).

Those of skill in the art will appreciate that adjustments to the array geometry can be made, i.e., sensor dimensions and sensor spacing. Vibrational energy 110 includes shear wave energy propagation with shear wavelengths on the order of several tens of millimeters, e.g. approximately 40 millimeters at 200 cycles per second and approximately 20 millimeters at 500 cycles per second.

Figure 1B:
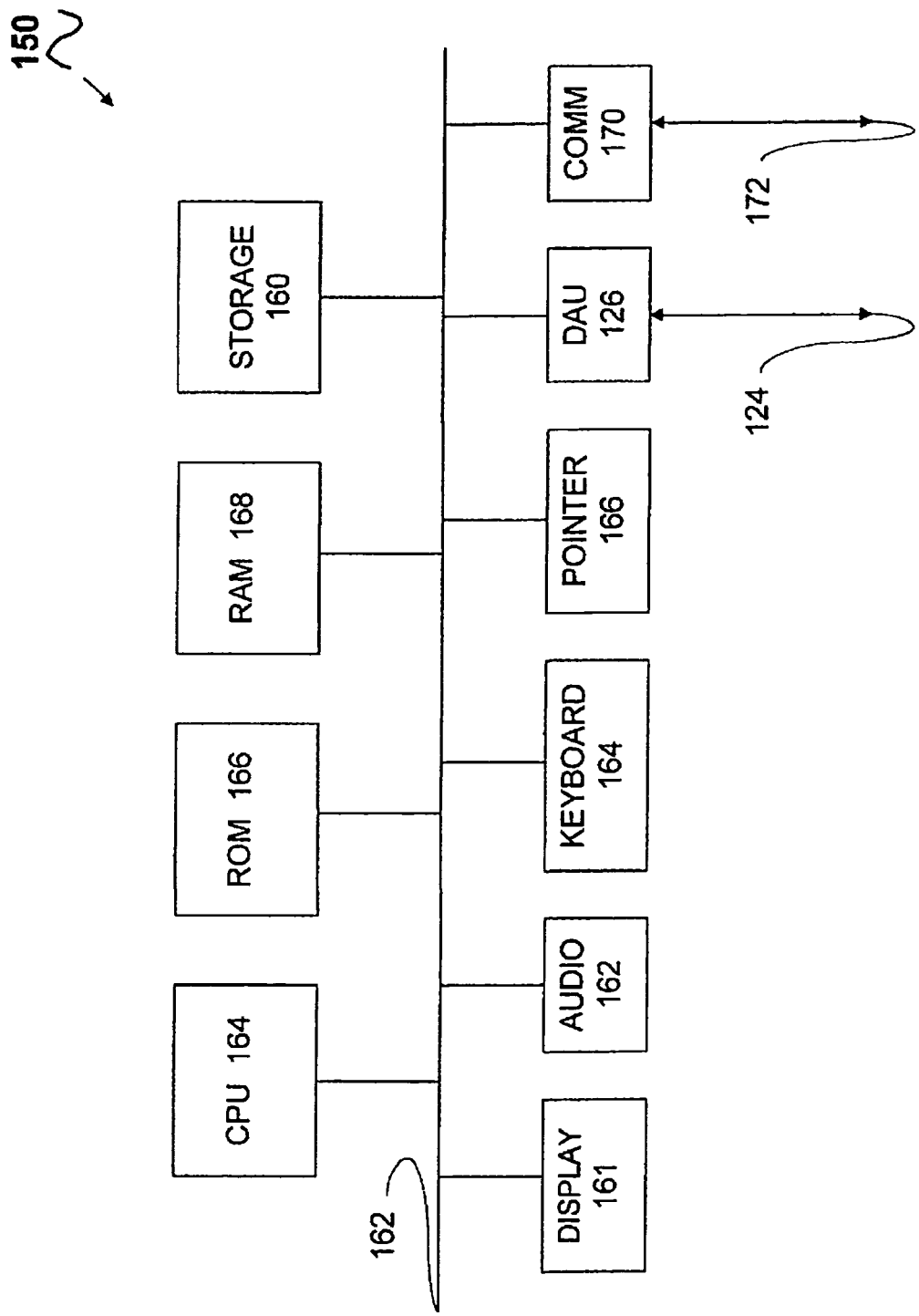
FIG. 1B illustrates a block diagram of a computer system (data acquisition system) in which embodiments of the invention may be used.

FIG. 1B illustrates, generally at 150, a block diagram of a computer system (data acquisition system) in which embodiments of the invention may be used. The block diagram is a high-level conceptual representation and may be implemented in a variety of ways and by various architectures. With reference to FIG. 1B, bus system 162 interconnects a Central Processing Unit (CPU) 164, Read Only Memory (ROM) 166, Random Access Memory (RAM) 168, storage 160, display

161, audio 162, keyboard 164, pointer 166, data acquisition unit (DAU) 126, and communications 170. The bus system 162 may be for example, one or more of such buses as a system bus, Peripheral Component Interconnect (PCI), Advanced Graphics Port (AGP), Small Computer System Interface (SCSI), Institute of Electrical and Electronics Engineers (IEEE) standard number 1394 (FireWire), Universal Serial Bus (USB), or a dedicated bus designed for a custom application, etc. The CPU 164 may be a single, multiple, or even a distributed computing resource. Storage 160 may be Compact Disc (CD), Digital Versatile Disk (DVD), hard disks (HD), optical disks, tape, flash, memory sticks, video recorders, etc. The computer system 150 can be used to receive vibrational cardiac data via 124 from the array 116 of vibration sensors (FIG. 1A). Note that depending upon the actual implementation of a computer system, the computer system may include some, all, more, or a rearrangement of components in the block diagram.

Thus, in various embodiments, vibrational cardiac data is received at 124 for processing by the computer system 150. Such data can be transmitted via communications interface 170 for further processing and diagnosis in a remote location, as illustrated in FIG. 1B at 172. Connection with a network, such as an intranet or the Internet is obtained via 172, as is recognized by those of skill in the art, which enables the data processing device 150 to communicate with other data processing devices in remote locations.

For example, embodiments of the invention can be implemented on a computer system 150 configured as a desktop computer or work station, on for example a WINDOWS® compatible computer running operating systems such as WINDOWS® XP Home or WINDOWS® XP Professional, Linux, etc. as well as computers from APPLE COMPUTER, Inc. running operating systems such as OS X, etc. Alternatively, or in conjunction with such an implementation, embodiments of the invention can be configured with devices such as speakers, earphones, video monitors, etc. configured for use with a Bluetooth communication channel.

Figure 2:
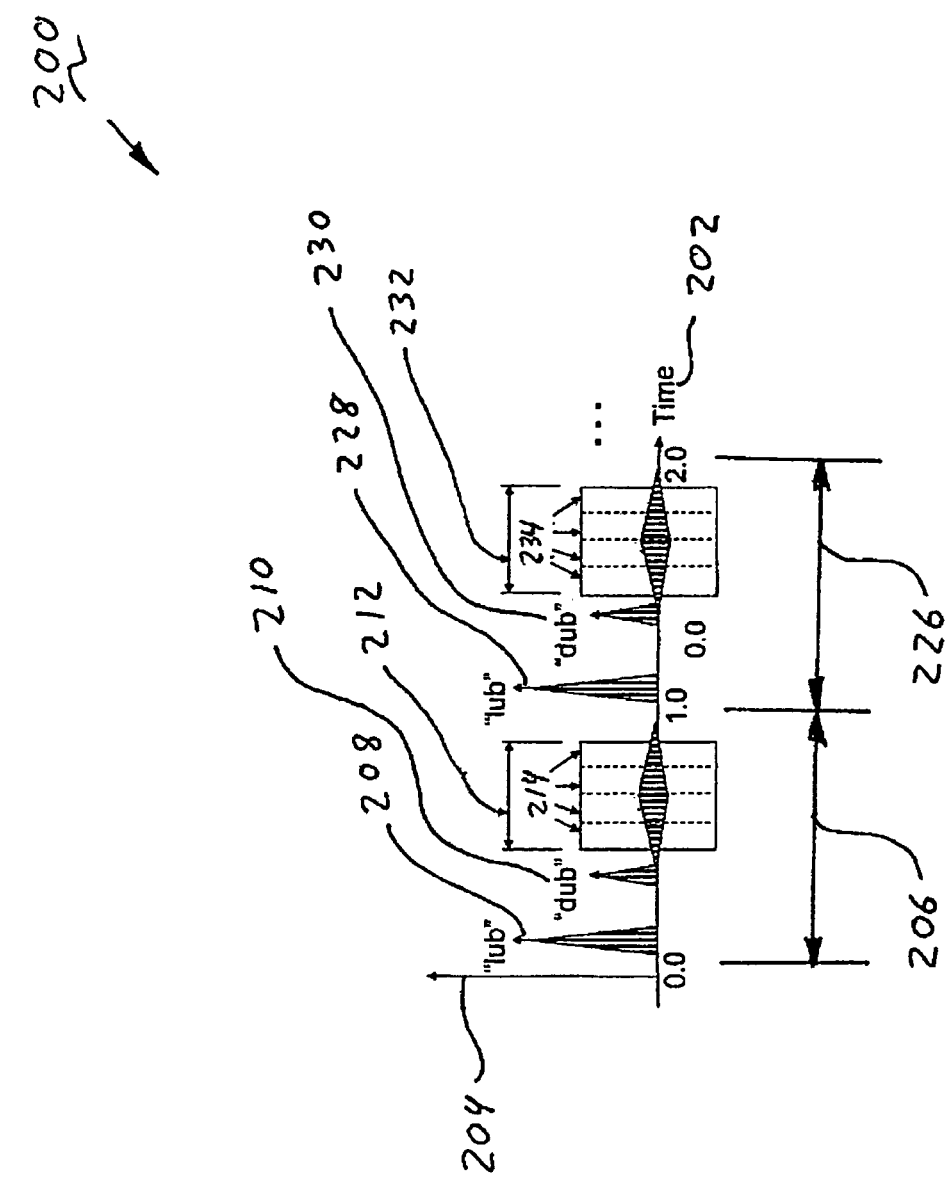
FIG. 2 illustrates a plot, representational of vibrational cardiac data as a function of time for two heart cycles, according to one embodiment of the invention.

FIG. 2 illustrates, generally at 200, a plot of vibrational cardiac data as a function of time for two heart cycles, according to one embodiment of the invention. With reference to FIG. 2, a representative output from one of the vibration sensors, from array 116 (FIG. 1A) is illustrated, where a magnitude of the sensor's output is plotted on a vertical axis 204 as a function of time 202. A first heart cycle 206 contains a first peak 208 corresponding to the closure of the mitral and tricuspid valves. This first peak is described in the literature as a "lub" sound when heard through a stethoscope. The first heart cycle 206 contains a second peak at 210, which corresponds to the closure of the two semi-lunar, aortic and pulmonary valves at the beginning of diastolic period 212. This second peak is described in the literature as a "dub" sound when heard through a stethoscope. The diastolic period 212 follows the second peak 210.

The heart continues to beat, and a second heart cycle 226 is produced thereby with the same major features found in the first heart cycle; a first peak at 228, followed by a second peak at 230, and a diastolic interval (DI) 232. Successive heart cycles (not shown) will continue to occur as the heart continues to beat. During the diastolic intervals, 212, 232, etc., blood flow is at a maximum in the coronary arteries and unwanted coronary events, such as the first peaks 208, 228 and the second peaks 210, 230 are separated in time and their effect on the diastolic interval is at a minimum.

In one embodiment, it is desirable to process vibrational cardiac data accumulated over approximately one hundred and twenty (120) heart cycles in order to provide a sufficiently long averaging time record length for an array of 14 channels. In practice, with human test subjects, it has been observed that the human test subjects can comfortably breath-hold for approximately twenty (20) heart cycles. In this case, a human test subject will alternate between breath-hold and normal breathing, for breath recovery, while the heart waveform is measured. In one embodiment, a nominal duration of the entire heart waveform is from one hundred and twenty (120) to one hundred and eighty (180) seconds and is made up of six (6) twenty (20) to thirty (30) second segments. In another embodiment, a number of heart cycles is approximately equal to ten (10) to fifteen (15) times the number of sensor channels in array N. Such a number of heart cycles is needed to adequately resolve the numerically higher eigenvalues as described below in sections of the following discussion. A shorter duration heart waveform (fewer heart cycles) can be collected if the eigenvalue range is limited accordingly. Those of skill in the art will appreciate that the entire heart waveform can vary in length and that the examples provided herein are given for illustration only and do not limit embodiments of the invention.

The number of heart cycles over which a human test subject can comfortably breath-hold will vary between human test subjects and will depend on many factors such as age, physical condition, etc. When vibrational cardiac data is collected during breath-hold, the effects of breathing on the measured vibrational cardiac data are minimized. The number of segments can be adjusted to suite the particular test conditions, given the length of time that the human test subject can breath-hold for and the number of sensor channels in the array N. In one embodiment, a human starts and stops the acquisition of the vibrational cardiac data to coincide with acquisition during breath-hold periods.

The N sensor array, described in FIG. 1A, is used to measure and process vibrational cardiac energy, which is measured at the surface 111 during the diastolic intervals. In one embodiment, such measurement and processing of the vibrational cardiac energy is used to determine whether a plaque deposit(s) (coronary artery lesion(s)) 108 exists in the human due to coronary artery disease. In other embodiments, such processing can be used to detect vibrational energy generated within the human in general and not necessarily caused by coronary artery disease.

Figure 3:
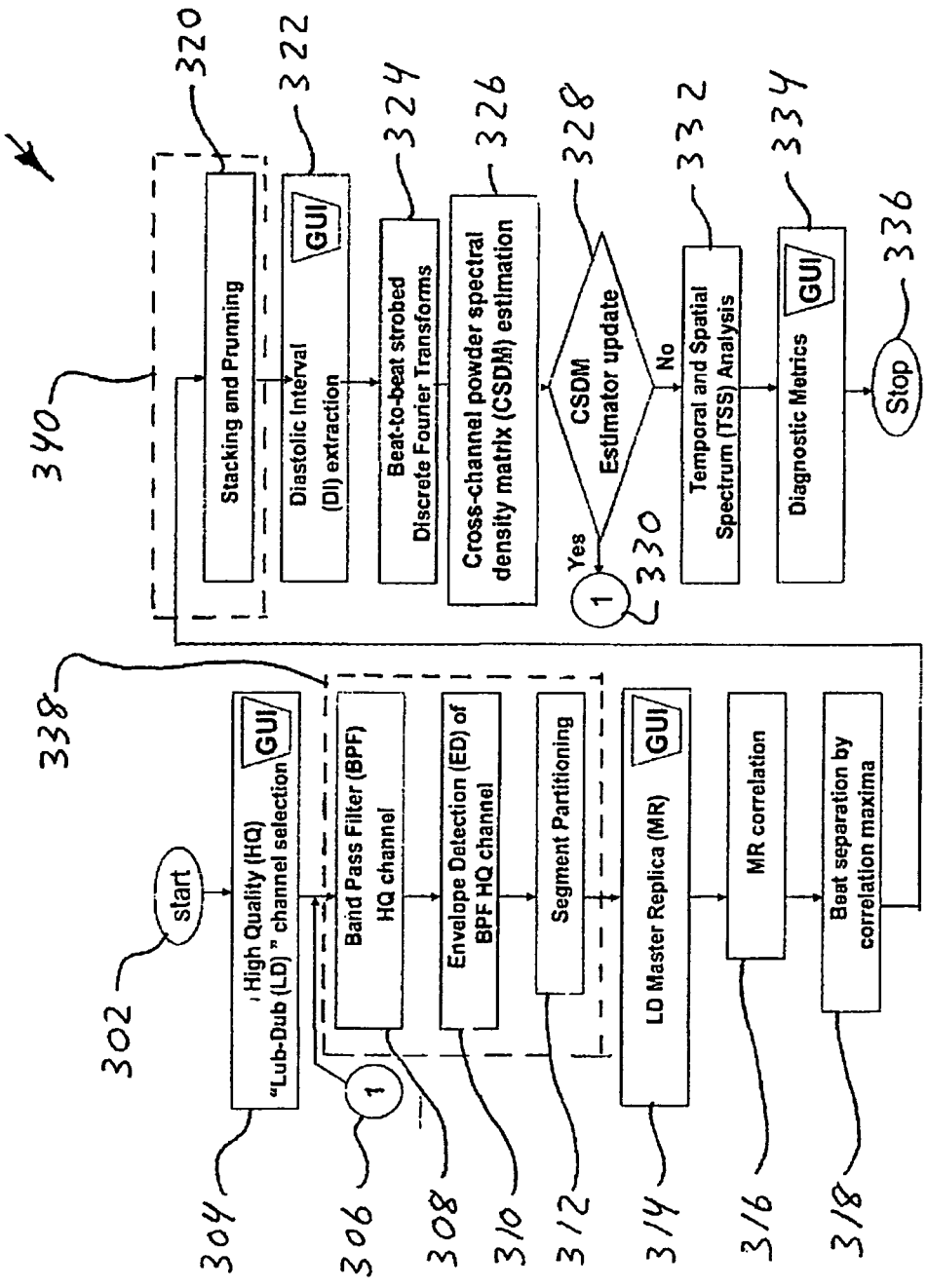
FIG. 3 illustrates a method for processing vibrational cardiac data, according to embodiments of the invention.

FIG. 3 illustrates, generally at 300, a method for processing vibrational cardiac data, according to embodiments of the invention. The method is applied to vibrational cardiac data that is measured with an array of N sensing transducers, which are mounted on the surface of a human's body as described above in conjunction with the previous figures. With reference to FIG. 3, a method starts at a block 302.

Figure 4:
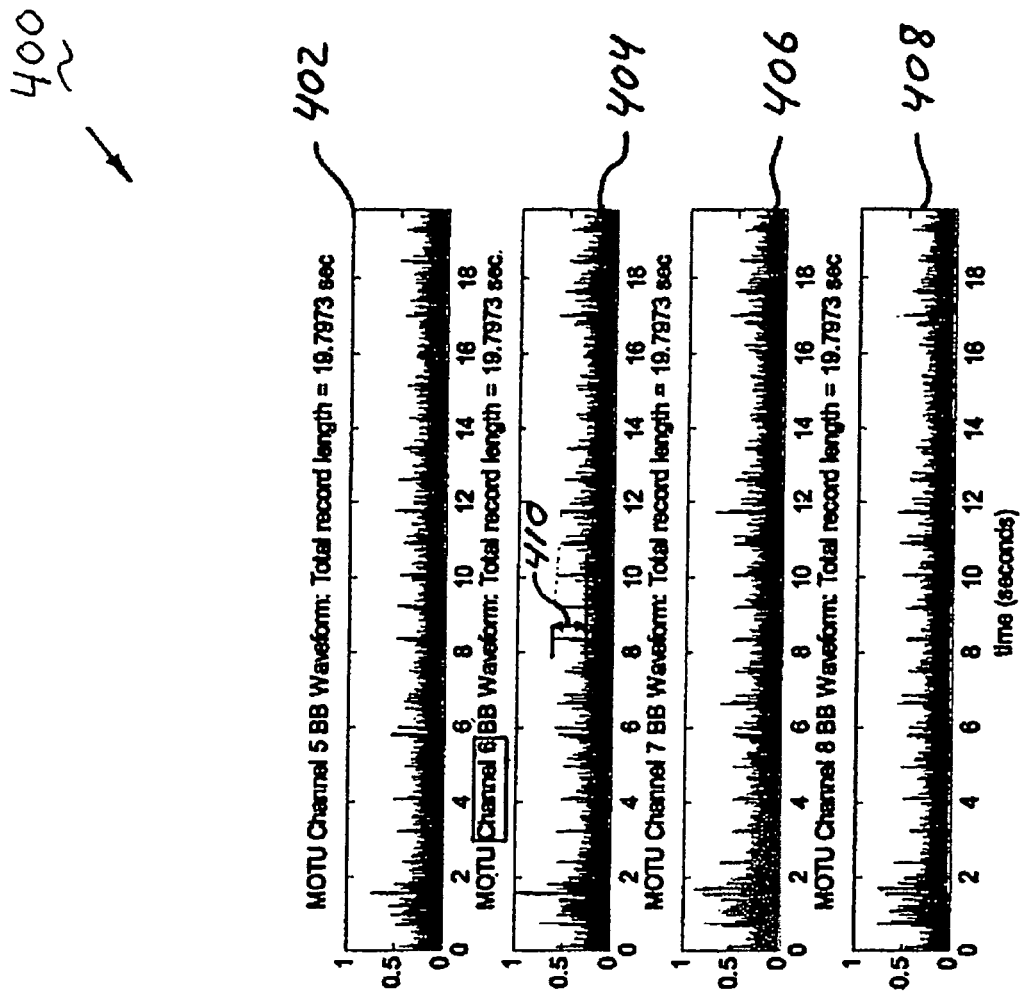
FIG. 4 illustrates several channels of vibrational cardiac data, according to an embodiment of the invention.

For the purpose of extracting diastolic intervals from their respective heart cycles, at a block 304 a technician selects a single high quality channel from the array of N sensing transducers. A high quality channel has a high signal-to-noise ratio, wherein the signal-to-noise ratio is expressed as the ratio between the height of a first peak of a heart cycle and the background level during the diastolic interval and the height of a second peak of the heart cycle and background level of the vibrational cardiac data. The selection of a high quality channel can be performed by a technician or it can be automated in a selection algorithm that would be performed by a data processing system such as the computer system (data acquisition system) described above in conjunction with FIG. 1B. FIG. 4 illustrates, generally at 400, several channels 402, 404, 406, and 408 of vibrational cardiac data according to an embodiment of the invention. In this example, Channel 6 indicated at 404 is selected as the high quality channel, with signal-to-noise ratio metric indicated at 410.

Optionally, at a block 308, the vibrational cardiac data from the high quality channel is band pass filtered to suppress energy at frequencies that are above and below the frequency content of the first and second peaks of the heart cycle. The band pass filter operation typically passes energy in the band from approximately 5 cycles per second (Hz) to several tens of Hz.

Optionally, at a block 310, envelope detection can be applied to the vibrational cardiac data from the high quality channel. Envelope detection operation is given by:

$$e(t)=\text{abs}(x(t)).$$

and can be performed before the band-pass filter operation of block 310. $x(t)$ is the high quality channel vibrational cardiac data time series, abs is the absolute value operator, and $e(t)$ is the envelope amplitude.

Optionally, one or more segments of heart cycle data can be collected to provide the entire heart waveform as described above. When multiple segments are collected, a master replica is selected from each segment.

With reference to FIG. 3, at a block 314, a master replica is selected from the high quality channel, which was specified at the block 304. The master replica is selected by selecting a heart cycle that is highly representative of a majority of heart cycles within the segment of the heart waveform represented by the high quality channel. The master replica is either a portion of or the entire heart cycle so identified. To illustrate the process, FIG. 4 displays vibrational cardiac data, generally at 400, collected from four (4) different transducer channels, i.e., a channel five (5) at 402, a channel six (6) at 404, a channel seven (7) at 406 and a channel eight (8) at 408. The vibrational cardiac data collected from channel six (6) at 404 (FIG. 4) will be used for master replica selection and correlation due to favorable signal-to-noise characteristics as indicated at 410.

Figure 5:
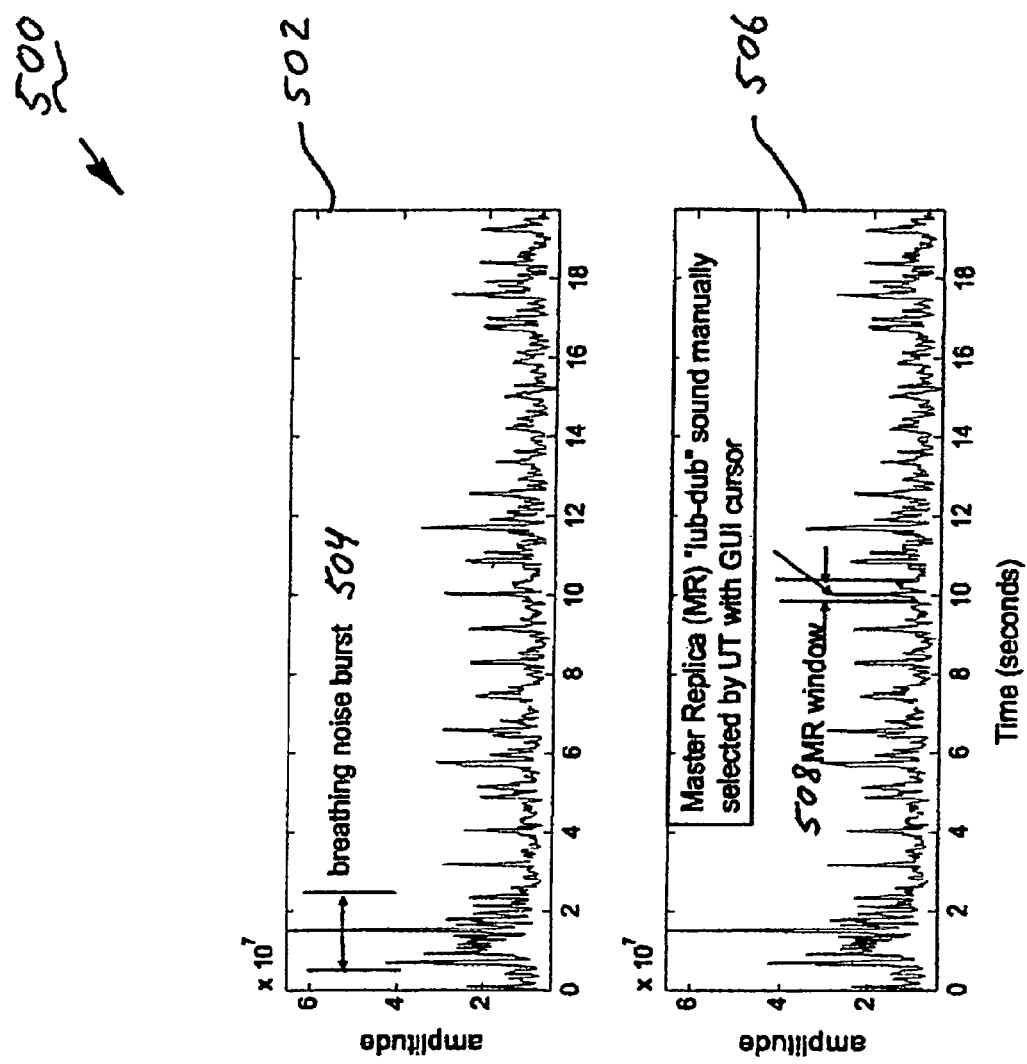
FIG. 5 illustrates master replica selection according to an embodiment of the invention.

Optionally, the data from 404 can be band-pass filtered, as described at the block 306 (FIG. 3) and is displayed as 502 in FIG. 5. FIG. 5 illustrates, generally at 500, master replica selection according to an embodiment of the invention. A noise burst due to breathing is marked at 504 and the same band-pass filtered data is displayed again at 506 where the master replica (MR) window is indicated at 508.

At a block 316 the master replica is correlated with the high quality channel vibrational cardiac data from which it was selected. This cross-correlation procedure produces a correlation waveform that is a function of the time lag between the master replica and the segment waveform extending over the entire length of the segment minus the time length of the master replica. The correlation waveform has local maxima when the master replica is temporally well aligned as a function of time lag with a corresponding high signal-to-noise ratio portion of the segment waveform. These local maxima establish time reference points that are used to identify the diastolic window and to align successive heart cycles in time, i.e., synchronize, for signal analysis.

Figure 6:
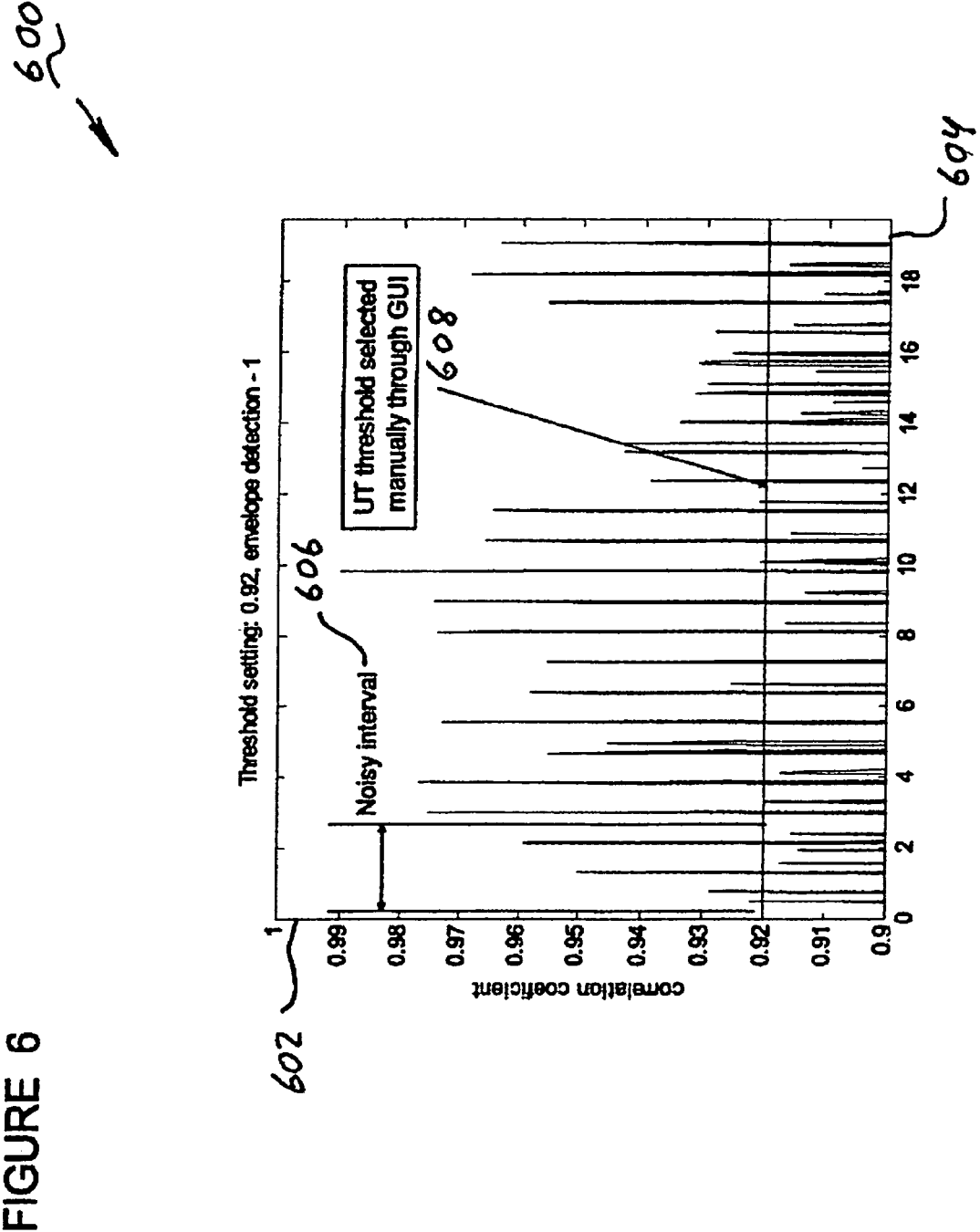
FIG. 6 illustrates, in one embodiment, a correlation scan.

At a block 318, the local maxima identified in the block 316 are used to separate heart cycles from a segment as a function of time. FIG. 6 illustrates, in one embodiment, a correlation scan, generally at 600, that resulted from the vibrational cardiac data shown at 506 in FIG. 5. With reference to FIG. 6, in one embodiment, the process begins by analyzing the correlation data 602 to locate local maxima for all values of time (t) for which the correlation coefficient $c(t)$ is:

$$c(t) > \max[c(t-1)c(t+1)].$$

Next, all values for which $c(t)$ falls below a threshold are discarded. With reference to FIG. 6, correlation coefficient $c(t)$ is plotted at 602 as a function of time 604. A threshold is indicated at 608. The threshold 608 can be defined by an operator with a graphical user interface (GUI) or it can be defined by the system.

Next, a time difference is obtained between a correlation peak and the peak that came before it in time. If the time difference is less than a threshold, then the maximum peak value is discarded as a possible heart beat cycle starting time. This process discards all candidate heart cycle starting times for heart cycles with a heart rate greater than a specified threshold. For example, a 0.5 second time difference threshold would disallow heart rates above 120 beats per minute (bpm). The local maxima that are left are used to identify the heart cycles from which the vibrational cardiac data will be extracted and processed. Generally lower values of correlation coefficient can be observed in interval 606 which correspond with the effects of breathing noise.

Figure 7:
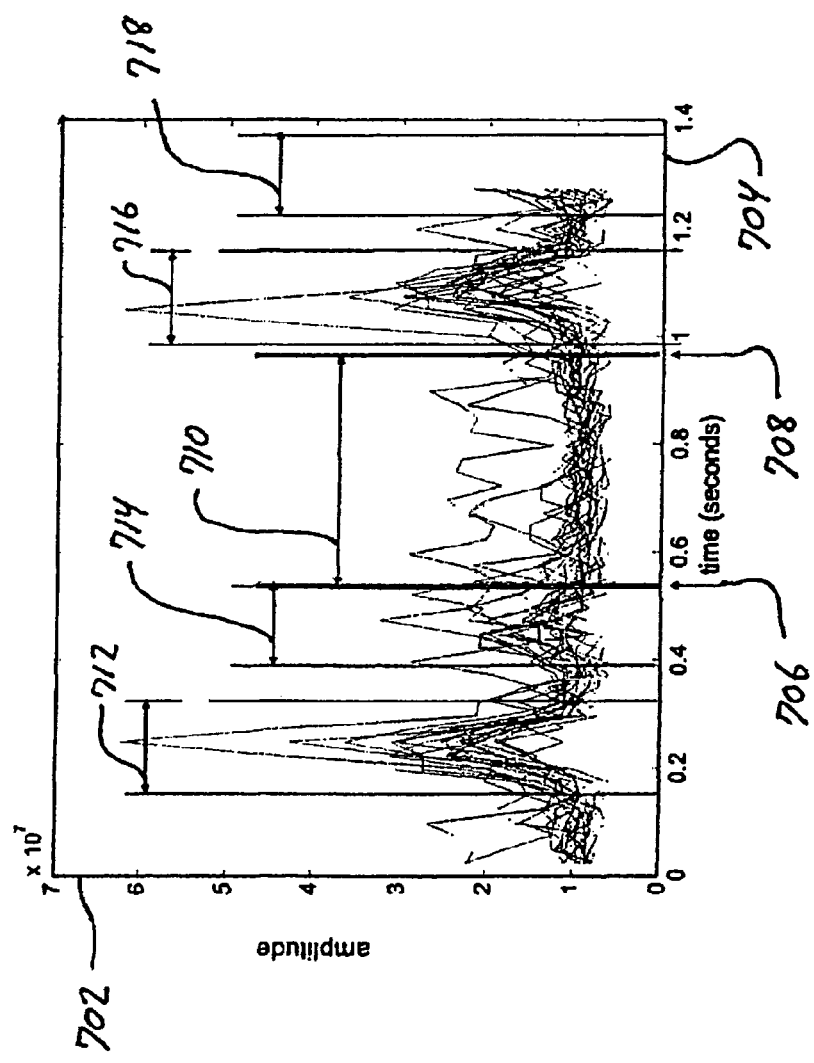
FIG. 7 illustrates, in one embodiment, assembling multiple heart cycles.

Corresponding with a block 320 (FIG. 3), FIG. 7 illustrates, in one embodiment, assembling multiple heart cycles. With reference to FIG. 7, the local maxima that are identified by the analysis described above in conjunction with the block 318 are used to define windows in time as the window starting times. The vibrational cardiac data corresponding to these windows in time are over plotted as illustrated, where amplitude is indicated on an axis 702 and time along an axis 704. Envelope amplitude maxima 712 and 714 are followed by a diastolic interval 710. Envelope amplitude maxima 716 and 718 are used to help the identification of the diastolic interval; however it is not mandatory to use all four Envelope amplitude maxima to locate the diastolic interval 710. A single envelope amplitude maxima and knowledge of the human's heart beat rate are sufficient to identify the diastolic interval 710. A start time 706 and a stop time 708 are placed at the ends of the diastolic interval either by a technician or these indicators can be located automatically by an algorithm in an automated process.

Optionally, for each of the diastolic intervals indicated at 710, a power parameter, such as average squared amplitude over the duration of the heart cycle is computed for each heart cycle. Then all of the average squared amplitude levels are averaged to produce a mean squared amplitude level averaged over all heart cycles over plotted. Each heart cycle's average squared amplitude level is compared to a multiple of the mean squared level and is discarded if its value exceeds the multiple of the mean squared level. In one embodiment the multiple is equal to 2.0. This heart cycle waveform pruning operation is used to discard those heart cycles that are contaminated by noise which is likely due to breathing and/or intestinal activity.

Figure 8:
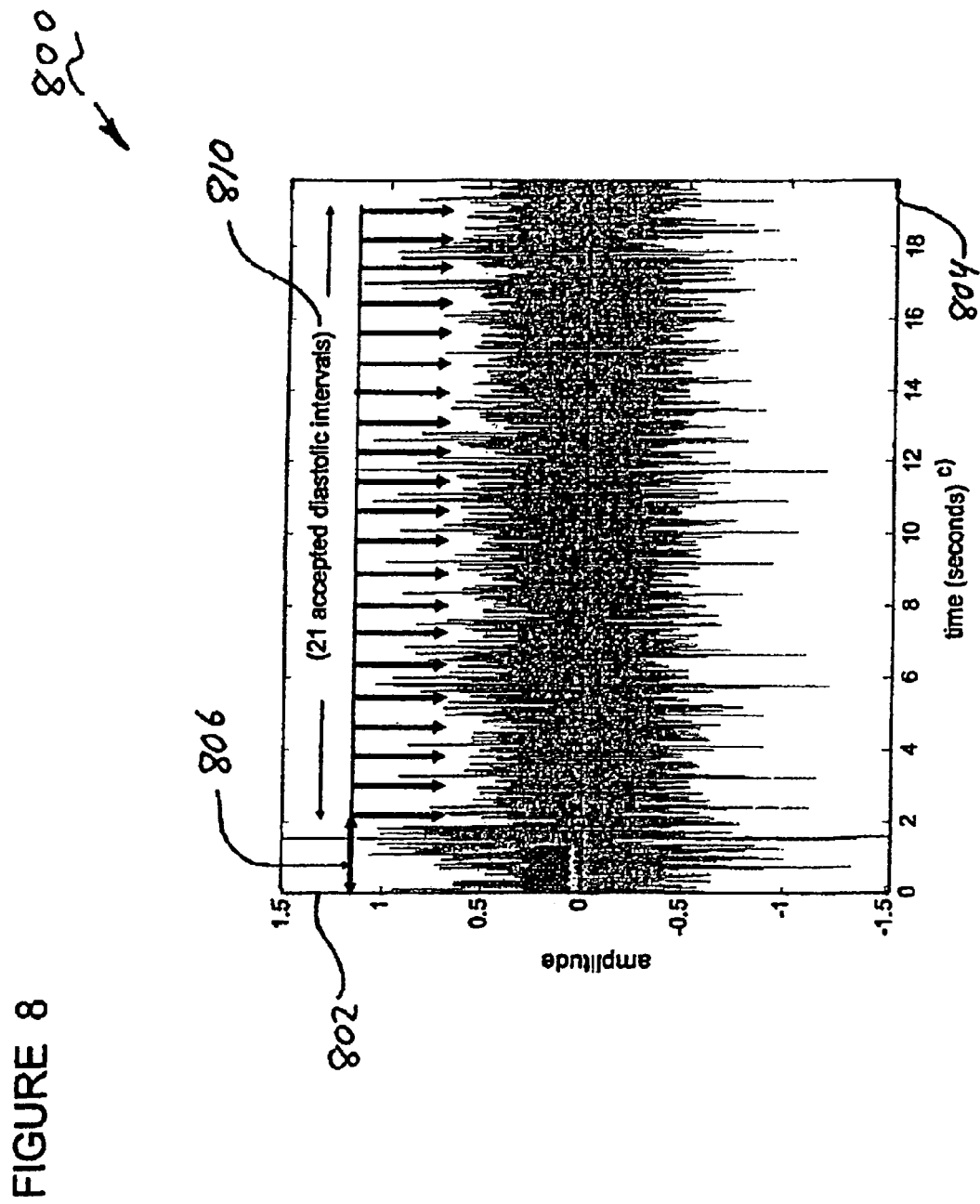
FIG. 8 illustrates, in one embodiment, diastolic intervals selected for further processing.

Corresponding with a block 322 (FIG. 3), FIG. 8 illustrates, in one embodiment; generally at 800, diastolic intervals selected for further processing. With reference to FIG. 8, using the heart cycle starting times, estimated above in conjunction with the previous figures, e.g., FIG. 7, a subsequence of adjacent time samples are extracted from the vibrational cardiac data 810. In FIG. 8, vibrational cardiac data from a high quality transducer channel are plotted with amplitude on an axis 802 and time on an axis 804. Vibrational cardiac data are accepted from 21 diastolic intervals. The intervals marked at 806 are contaminated with excessive noise and are rejected.

Corresponding with a block 324 (FIG. 3), the vibrational cardiac data that are extracted during the identical time window for all N sensors channels, from the diastolic windows, can be processed as a continuous ensemble of data or the diastolic window can be further partitioned into subintervals or slots as described above. Referring back to FIG. 2, the diastolic window 212 is divided into four 4 slots 214 and the next diastolic window 232 is partitioned into four (4) slots 234. Adjacent time slots with the slots 214 or 234 can overlap in time. The slots have fixed starting times relative to the respective diastolic interval and are typically separated by less than one tenth of an average heart cycle (for example, 0.1 seconds for a 60 beat per minute heart cycle). In one embodiment, the length of the slot interval, in number of time samples, is taken to be the number of points in a discrete Fast Fourier Transform (FFT) operation which is performed independently within each slot. This procedure effectively strobes the same time slot number (e.g. 1, 2, 3, 4, etc.) from each heart cycle for FFT spectrum analysis. In various embodiments, the temporal length of an FFT window slot is in the range of 0.15±0.1 seconds. Thus, for each sensor channel, a complex Fourier spectrum of the vibrational cardiac data is computed from the time series data.

Figure 9:
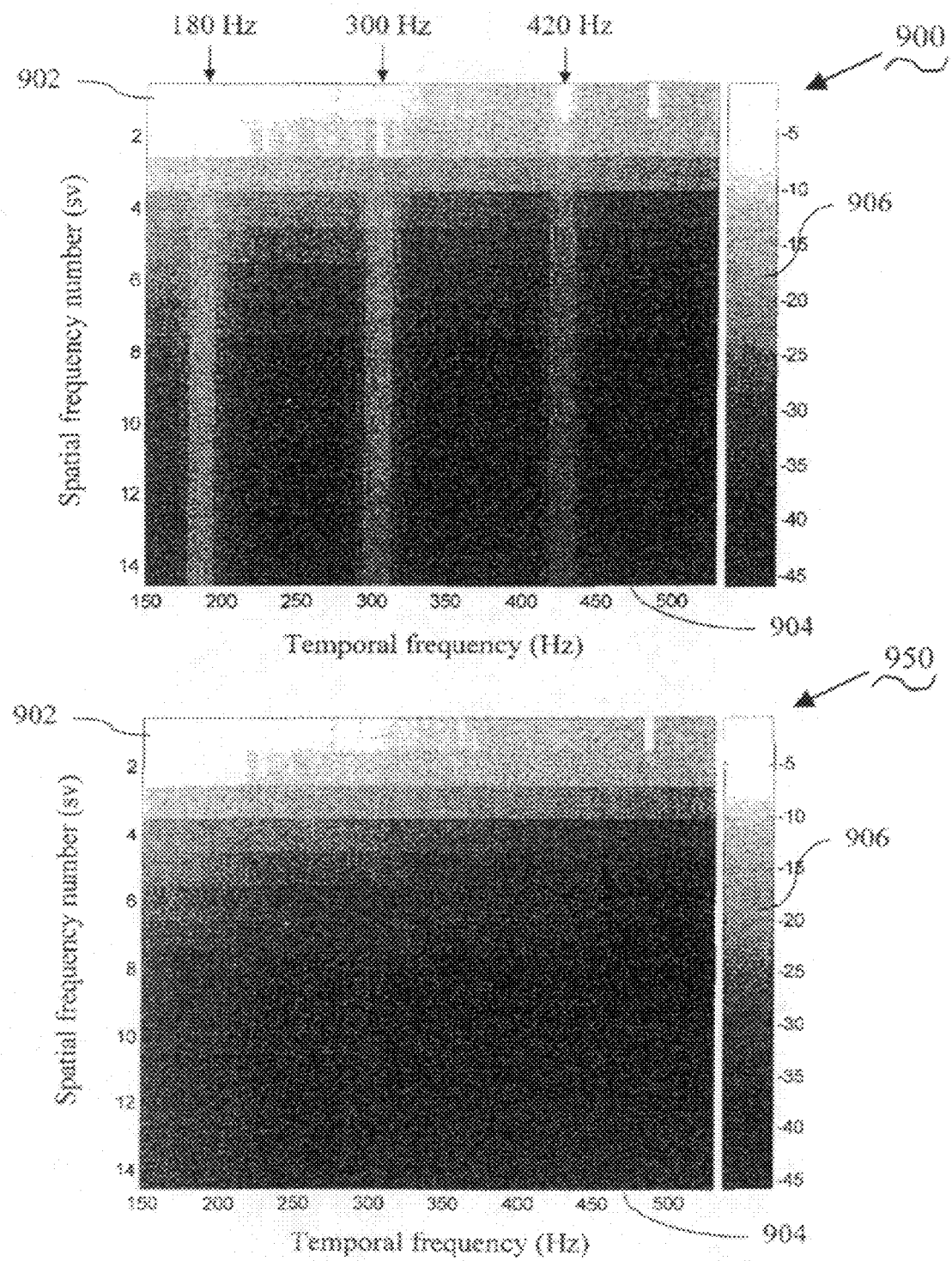
FIG. 9 illustrates a two-dimensional space-time frequency power spectrum (orthogonal vibration mode decomposition of the cross-channel power spectral density matrix "CSDM") of vibrational cardiac data, rendered as a grey scale image according to one embodiment of the invention.

Corresponding with a block 326 (FIG. 3), FIG. 9 illustrates a two-dimensional space-time frequency power spectrum (cross-channel power spectral density matrix "CSDM") of vibrational cardiac data, generally at 900, according to one embodiment of the invention. With reference to FIG. 9, spatial frequency number is plotted on an axis 902 and temporal frequency is plotted on an axis 904. Normalized amplitude is indicated by a grey scale color and a reference key is illustrated at 906.

The CSDM is either computed for the entire heart cycle, based on averaging all heart cycles in the entire heart waveform or it can optionally be computed for the a specific slot number in the heart cycle. In either case, the CSDM is computed by placing the complex Fourier spectrum (FFT outputs), obtained by processing the transducer channel outputs, into a four-dimensional matrix indexed as x(n, b, k, m):

$$x(b, k, m) = \begin{bmatrix} x(1, b, k, m) \\ x(2, b, k, m) \\ \vdots \\ x(N, b, k, m) \end{bmatrix}$$

where n is the vibration transducer number, k is the FFT discrete frequency bin number, b is the retained heart beat count, and m is the slot number. In cases where a heart waveform contains multiple segments, heart beat count b will span multiple time segments, where each segment corresponds to a breath holding period as described above.

With N as the number of vibration transducer channels, the CSDM is then an N-by-N complex Hermitian R(k, m) matrix. R(k, m) is calculated as a time average over the heart beat count index b, separately for each frequency bin k, and slot number m, according to:

$$R(k, m) = \frac{1}{B} \sum_{b=1}^{B} x(b, k, m) * x(b, k, m)'$$

Where B is the number of heart beat cycles in the averaging ensemble which can span multiple segments of acquired vibrational transducer data in some embodiments. The value of B will depend on the number of separate transducer channels processed for a given measurement. Generally, a lower bound for the value of B is approximately four (4) times the number of transducers, N. A preferred value for B is eight (8) to ten (10) times N. Those of skill in the art will recognize that the goal in selecting the value for B is to reduce the variance in the estimation of the CSDM matrix, therefore the value of B can be set at various numbers and the values of eight (8) to ten (10) are illustrative and not limiting.

Corresponding with a block 328 (FIG. 3), the processes from a block 306 to the block 326 are repeated as needed for each segment in the heart waveform. Thus, if the heart waveform contains more than one segment, control transfers from 330 to the block 306 and the intervening process blocks are repeated. Note, that for each segment in the heart waveform, a new master replica is chosen and a correlation step is performed on a segment-by-segment basis. This process accommodates variations in heart rate within a segment and the time averaging in the CSDM process (block 326) spans the time epoch for all segments acquired and processed within a heart waveform.

Figure 10:
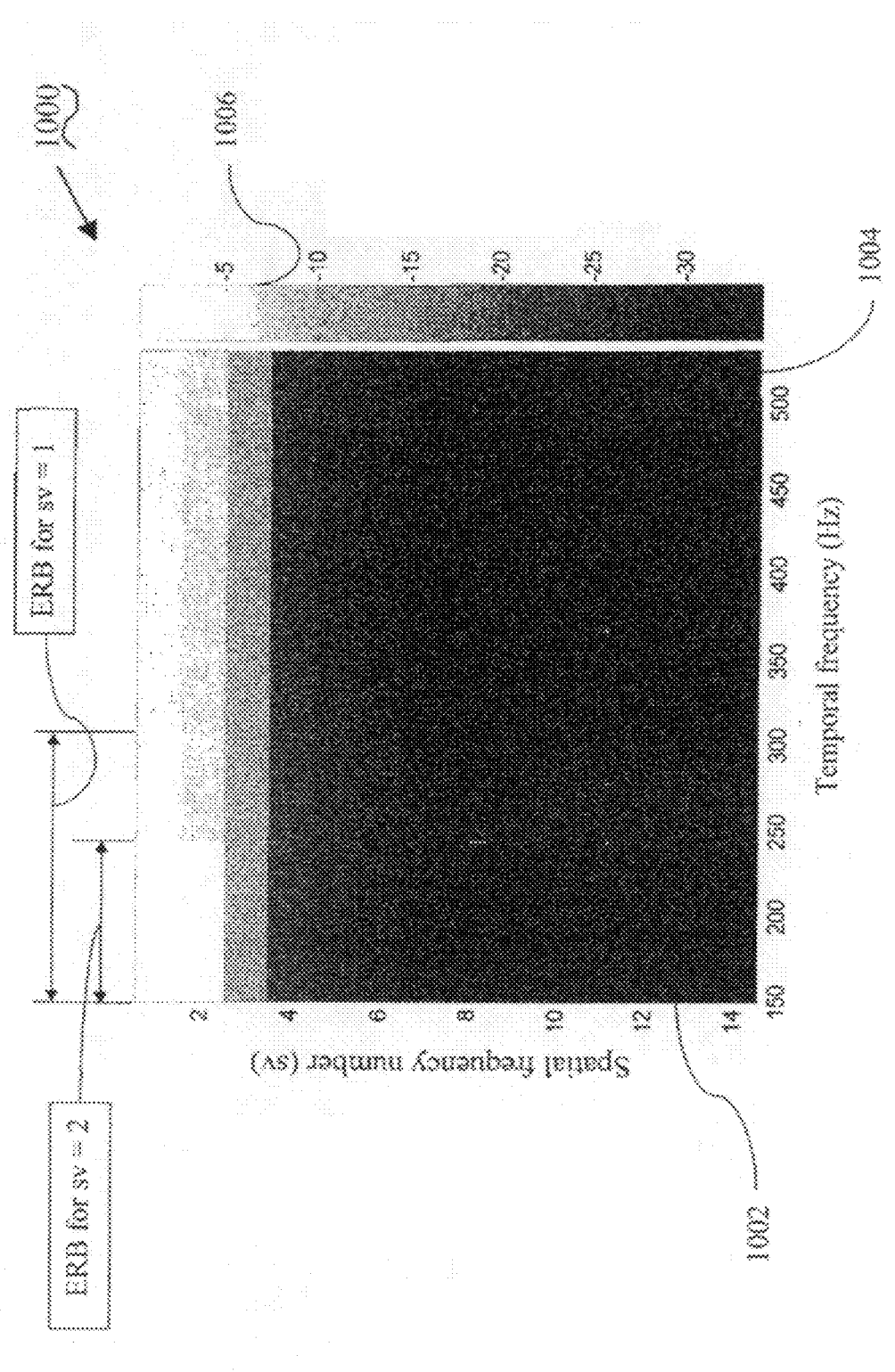
FIG. 10 illustrates a two-dimensional space-time frequency power spectrum processed for Equivalent Rectangular Bandwidth, rendered as a grey scale image according to one embodiment of the invention.

Corresponding with a block 332 (FIG. 3), FIG. 10 illustrates a two-dimensional space-time frequency power spectrum (Temporal-Spatial Spectrum (TSS)) processed for Equivalent Rectangular Bandwidth (ERB), generally at 1000, according to one embodiment of the invention. With reference to FIG. 10, temporal frequency is plotted on an axis 1004 and eigenvalue number/index (Spatial frequency number (sv)) is plotted on an axis 1002. Relative amplitude 1006 of the data is displayed as a modulation of gray scale. Following completion of the CSDM calculation (block 330), an eigenvalue-eigenvector decomposition (EED) of the CSDM in each slot and for each FFT frequency bin in the range $k_{low} \leq k \leq k_{high}$ is computed. This decomposition of the CSDM provides estimates of the blood flow turbulence induced noise spectrum level and bandwidth.

With N transducer channels, the distribution of energy in the CSDM eigenvalues at each frequency also quantifies the degree of angular concentration of spatial radiation points. The metric of spatial distribution of energy sources is referred to herein as spatial bandwidth and is non-parametric since it does not require a propagation model parameterization, including wave speed, of the non-homogeneous body medium 112 (FIG. 1A) through which the wave energy propagates from the turbulent induced noise location within the artery (FIG. 1A).

The EED is calculated according to:

$$[M(k,m), L(k,m), M(k,m)] = svd(R(k,m))$$

where M(k, m) is the N-by-N matrix of orthonormal eigenvectors of (R(k, m) as columns and L(k, m) is the diagonal matrix of corresponding eigenvalues arranged in monotonically decreasing order from the upper left to lower right.

In one embodiment, to establish a noise floor for the analysis, the smallest $N_f$ eigenvalues are averaged over all FFT frequency values and then these frequency averages are in turn, averaged over the smallest $N_f$ values. This produces a two dimensional space-time average. The number $N_f$ is typically ten to thirty percent of the total number of transducer channels, N, and the frequency bins over which frequency averaging is performed are within the range above 100. This two dimensional averaged eigenvalue, $\lambda_0$, is termed the TSS noise floor. The TSS noise floor sets a threshold, over which an accumulation (summation) of eigenvalues is performed. This accumulation of eigenvalues contains an estimate of the blood flow turbulence induced noise energy.

For the largest p=1, 2, 3, ..., N–$N_f$ eigenvalues, all of the eigenvalues as a function of frequency for a fixed value of p that exceed a threshold given by $\alpha\lambda_0$ are counted by integer counter $C_{s(p)}$ and averaged as $\lambda_{s(p)}$ and those that do not exceed the threshold are counted by $C_{n(p)}$ also averaged as $\lambda_{n(p)}$.

Referring back to FIG. 9, the CSDM eigenvalues are plotted along the vertical axis as a function of frequency (horizontal axis) for the sample case described herein. The estimation of the CSDM presented in FIG. 9 has been obtained by time averaging the "slot 1" interval processed data over five segments with a total of ninety (90) heart cycles. The $3^{rd}$, $5^{th}$, and $7^{th}$ harmonics of the 60 cycle power line artifact are evident in the data. Subsequently, these artifacts are nulled, blocked, and extrapolated through, which effectively notches out the FFT frequency bins as illustrated in the image at 950. Similar processing can be performed on the other slots within the diastolic interval.

Corresponding with a block 334 (FIG. 3), referring back to FIG. 10, The counter $C_{s(p)}$ when multiplied by the FFT frequency bin width (equal to the numerical inverse of the FFT interval in seconds) is termed the Equivalent Rectangular spectral Bandwidth, ERB, for spatial eigenvalue p. The estimated number set $C=[C_{s(p)}, \lambda_{s(p)}, C_{n(p)}, \lambda_{n(p)}, \alpha, \lambda_0$ for p=1, 2, . . . , N–N_d] can provide a diagnostic tool for the detection of arterial blood flow turbulence and thereby the causative pathology. A simulation of such detection was performed on a phantom and is described below in conjunction with FIG. 11 through FIG. 14.

Referring back to FIG. 10, presentation of the set C in relative terms, shows that the magnitudes of the temporal frequency bandwidth counter $C_{s(p)}$ and the Signal-to-Noise Ratio (SNR) metric ($\lambda_{s(p)}/\lambda_0$) are in proportion to and therefore a positively correlated marker for blood flow turbulence. In addition, the extent to which the threshold is crossed for larger values of p is in proportion to the extent of spatial distribution, i.e. spatial bandwidth, of the arterial occlusions that result in blood flow turbulence.

In other embodiments, different algorithms can be used to express Equivalent Rectangular Bandwidth (ERB). All such expressions maintain both long-time averaged and spatial-temporal spectrum analysis of the signals from an array of vibration sensors. In one such alternative embodiment, the temporal eigenvalue spectrum for each spatial frequency index, $L(k, p)$, $k_{low} \leq k \leq k_{high}$, for each spatial frequency index, p, is searched over the temporal frequency index k for the point at which the level has decreased to a pre-specified value (e.g. –3 db, –6 db, . . . ) relative to the maximum value. This embodiment is appropriate where the shape of the eigenvalue spectrum has a monotonically decreasing trend with increasing k.

The process begins by pre-smoothing the estimated frequency spectrum as a least squares fit of log $10(L(k, p))$ to a two parameter linear function over the range of k. Such smoothing permits a specific value of $k=C_{s(p)}$ at the specified reduced value threshold point relative to the maximum value, log $10(L(k_{low}, p))$, to be identified. Given the estimated value of $k=C_{s(p)}$ at the specified reduced value level threshold, for each of p=1, 2, . . . , N, the eigenvalues as a function of frequency, k, that exceed the threshold are given by the averaged value above the threshold as $\lambda_{s(p)}$ and those that do not exceed the threshold are counted by $C_{n(p)}$ and expressed by the averaged value below the threshold as $\lambda_{n(p)}$.

In this alternative embodiment, the estimated number set $C'=[C_{s(p)}, \lambda_{s(p)}, C_{n(p)}, \lambda_{n(p)}$, for p=1, 2, . . . , N] or its functional equivalent, can be used with appropriate human data to provide a diagnostic tool for the detection of arterial blood flow turbulence and the causative pathology. An example of such use is illustrated below in conjunction with FIG. 11 through FIG. 14.

Examination of the set C', shows that the magnitudes of the temporal frequency bandwidth counter $C_{s(p)}$ and the Signal-to-Noise Ratio (SNR) metric ($\lambda_{s(p)}/\lambda_{n(p)}$) are in proportion to and are therefore a positively correlated marker for the presence of blood flow turbulence. This alternative embodiment can be generalized by performing higher order approximations to the estimated eigenvalue spectrum and thereby increasing the number of parameters subjected to a diagnostic process. On this issue, the example presented above embodies the lowest possible complexity.

Figure 11:
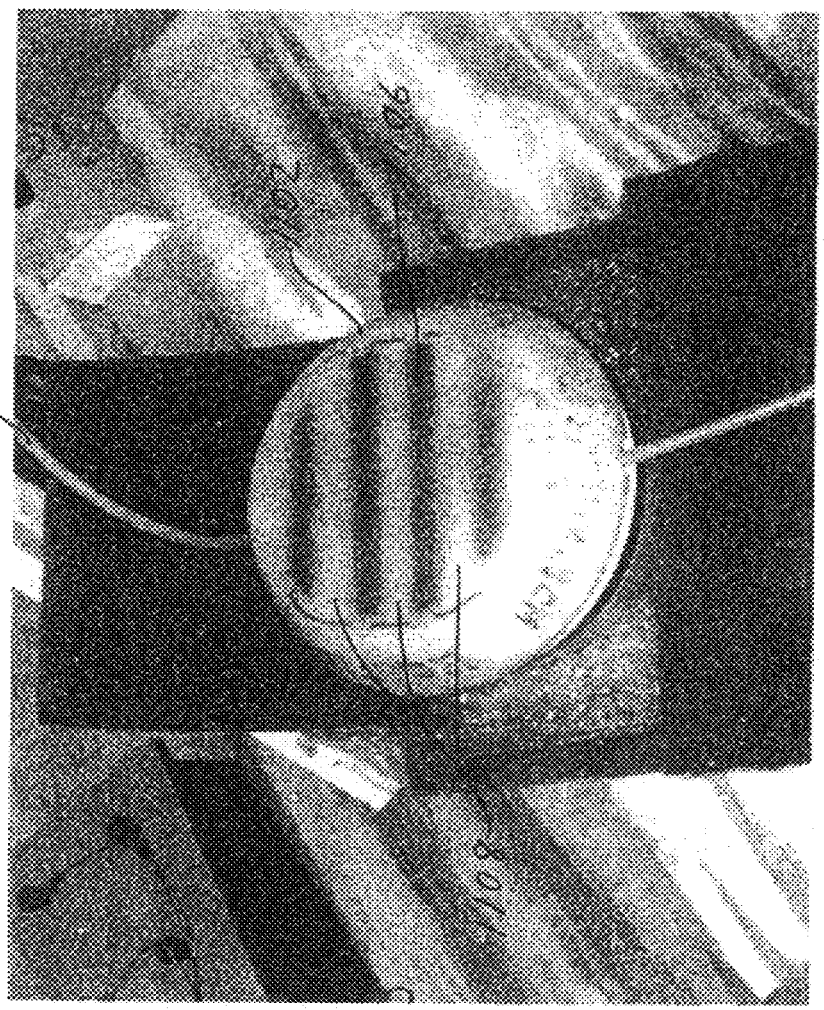
FIG. 11 illustrates a phantom constructed to simulate blood flow through an area of stenosis, rendered as a grey scale image according to one embodiment of the invention.

FIG. 11 illustrates a phantom, generally at 1100, constructed to simulate blood flow through an area of stenosis, according to one embodiment of the invention. With reference to FIG. 11, a phantom simulator of the human thorax 1102 in the vicinity of the chest wall was formed from silicone gel 1106 with a predetermined stiffness comparable to human tissue. The phantom contained high-stiffness human rib surrogates 1108 made of shaped plastic. Blood flow was simulated within a latex tube 1104 having cross-sectional characteristics typical of the left anterior descending (LAD) human coronary artery with a 3.0 millimeters (mm) inner diameter. Fluid flow occluders of different topologies were inserted into the latex tubing and the blood was simulated in viscosity with mixtures of 25 to 50% glycol and distilled water. All dimensions were known and the latex tube was embedded at a depth of 40 mm from the contiguous surface of the phantom.

The long axis of the vibration sensor linear array (not shown) was placed parallel to the rib surrogates 1108 and directly over the linear space between a pair of the rib surrogates 1108. Such placement simulates placement on a human and established a direct vibration wave path from the induced turbulent flow site to the vibration sensors located on the contiguous surface of the phantom.

Figure 12:
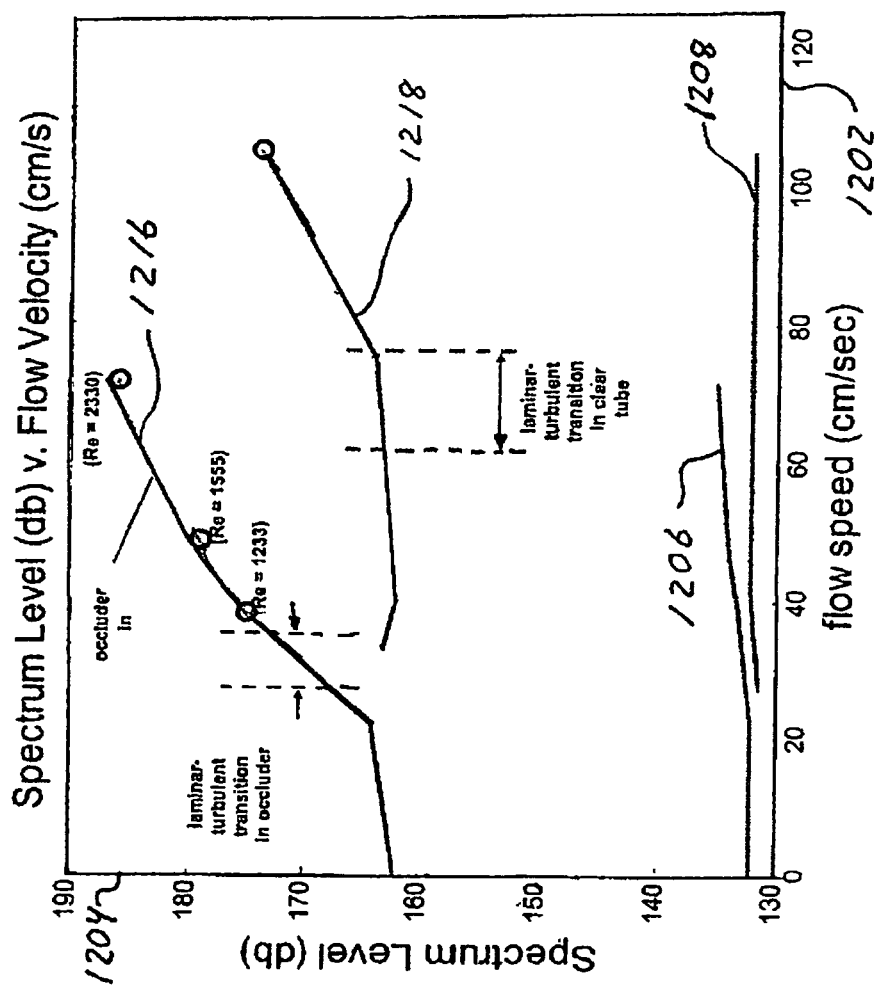
FIG. 12 illustrates detection of stenosis in a phantom, according to embodiments of the invention.

FIG. 12 illustrates detection of stenosis occlusion in a phantom, generally at 1200, according to embodiments of the invention. With reference to FIG. 12, the measured power spectrum level of vibration transducers is plotted on a vertical axis 1204. Spectrum level represents an integration in frequency of the energy in a given eigenvalue. Flow speed is plotted on an axis 1202. A series of experiments were conducted with different flow speeds with and without an occluder present in the latex tube 1104 (FIG. 11) to simulate an area of stenosis in a human.

One experiment consisted of comparing the case of a high flow rate, 72 cm/sec, without occluder (to induce turbulence) to a realistic human diastolic LAD flow rate, 35 cm/sec, with occluder induced flow turbulence (to simulate stenosis in a human). The higher flow rate had more than four times the laminar flow kinetic energy than the lower flow rate wherein turbulence was induced by the occluder. The objective of this experiment was to quantify the vibrational energy levels from both flow regimes and to evaluate the sensitivity of the methods described herein as a procedure for discriminating phantom simulated pathological flow from normal unoccluded flow (healthy no stenosis) at a very high level in order to produce a worst case detection scenario.

FIG. 12 shows the Measured Power Spectrum level (relative decibels, db) versus fluid flow rate (cm/sec) for flow "with occluder" at 1216 and "without occluder" at 1218. Plotted in FIG. 12 are the maximum and minimum eigenvalues, sv01 and sv14, respectively, of the 14 sensor array estimated Cross-Spectral Density matrix (CSDM). Eigenvalue sv14 is shown at 1206 with occluder and at 1208 without occluder. Eigenvalue sv01 is plotted at 1216, as a function of flow speed, with occluder in to simulate an area of stenosis.

Eigenvalue sv01 is plotted at 1218 without occluder to simulate the healthy state, free of stenosis.

FIG. 12 illustrates that the vibrational energy detected at the surface of the phantom is larger in all cases, with the occluder present and low flow rate, than even the very high 100 cm/sec flow rate with no occluder present. Of particular interest for detecting stenosis in humans is the condition of occluded flow (1216) for velocities above 40 cm/sec, the detected levels remain above that for unoccluded flow (1218) even at a flow velocity of 100 cm/sec. Such results demonstrate a capability for discrimination between even very high flow rates without occluder induced noise (1218) and nominally low flow rates with occluder produced turbulence (1216).

Figure 13:
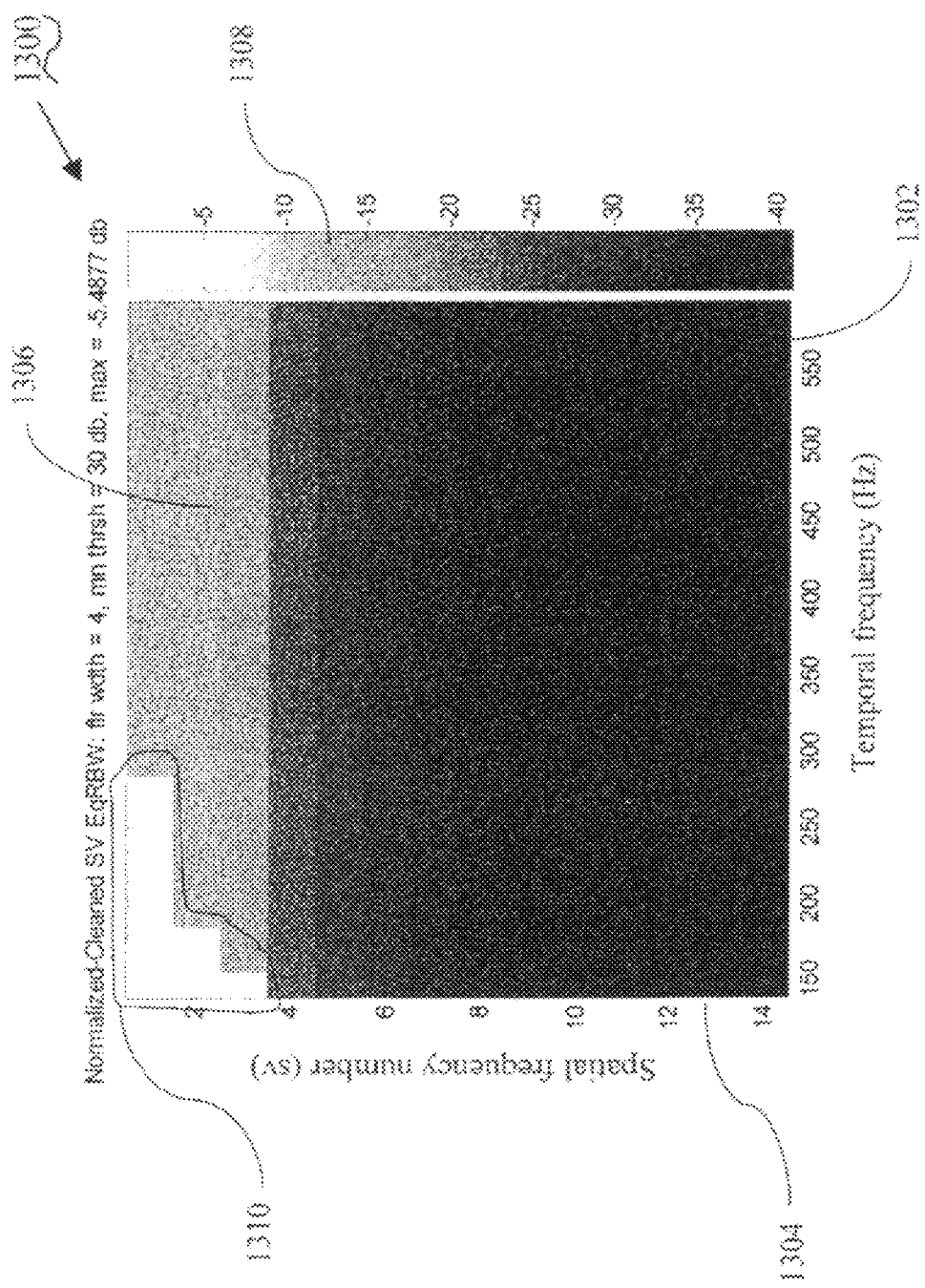
FIG. 13 illustrates an Equivalent Rectangular bandwidth (ERB) display of vibrational energy resulting from fluid flow with occluder present in a phantom (area of stenosis), rendered as a grey scale image according to one embodiment of the invention.

FIG. 13 illustrates an Equivalent Rectangular bandwidth (ERB) display of vibrational energy resulting from fluid flow with occluder present (area of stenosis), generally at 1300, according to one embodiment of the invention. With reference to FIG. 13, temporal frequency is plotted on an axis 1302 and eigenvalue number/index is plotted on an axis 1304. Relative amplitude 1308 of the data 1306 is displayed as a modulation of gray scale. Data 1306 represents an Equivalent Rectangular Bandwidth (ERB) estimate for the 35 cm/sec flow rate with an occluder present.

Figure 14:
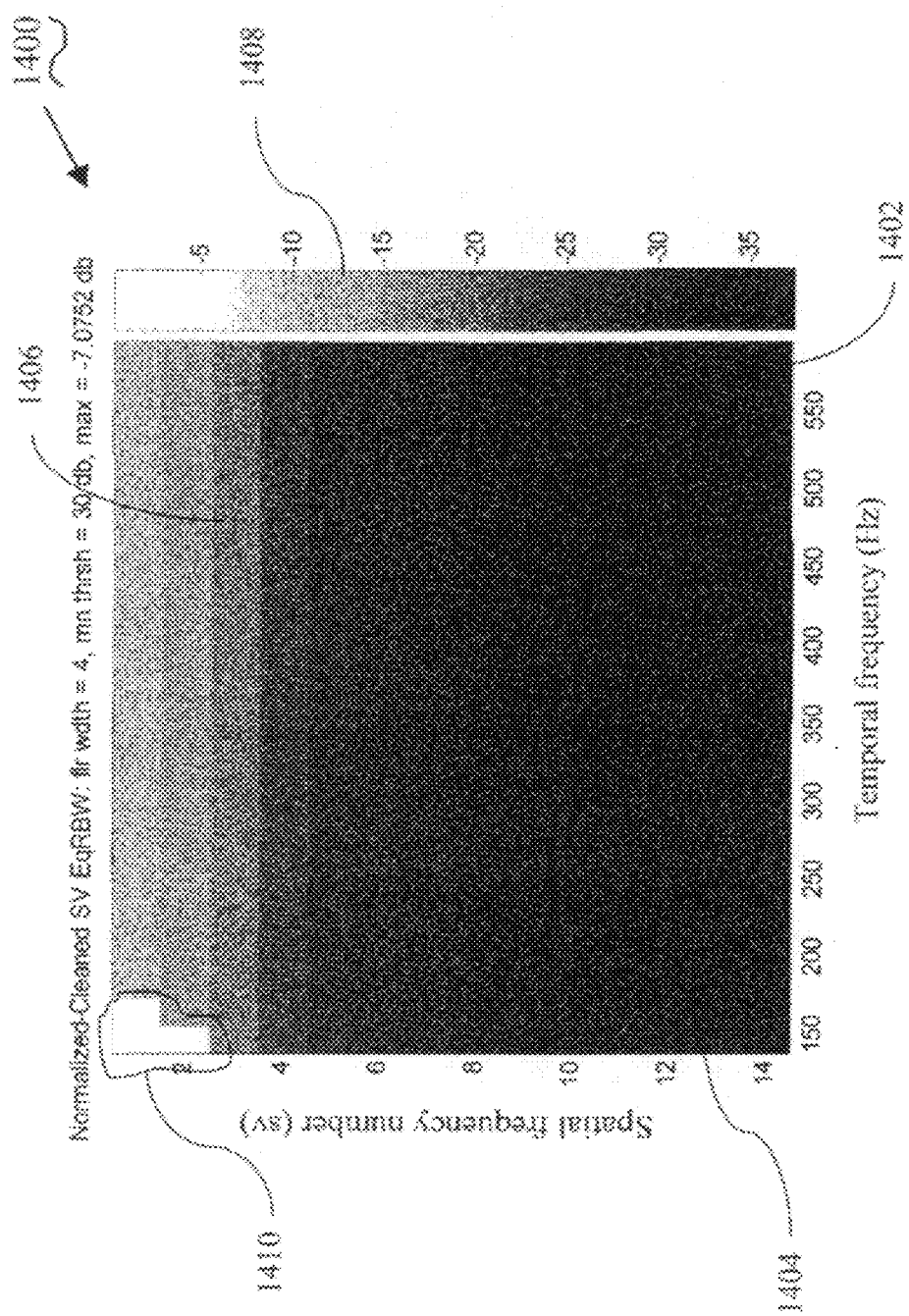
FIG. 14 illustrates an Equivalent Rectangular bandwidth (ERB) estimate of vibrational energy resulting from fluid flow without occluder in a phantom (healthy condition without stenosis), rendered as a grey scale image according to one embodiment of the invention.

FIG. 14 illustrates an Equivalent Rectangular bandwidth (ERB) estimate of vibrational energy resulting from fluid flow without occluder (healthy condition without stenosis), generally at 1400, according to one embodiment of the invention. With reference to FIG. 14, the same format is used to present the data from the 14 channel array, temporal frequency is plotted on an axis 1402 and eigenvalue number/index is plotted on an axis 1404. Relative amplitude 1408 of the data 1406 is displayed as a modulation of gray scale. The flow rate of the simulated blood flow was 72 cm/sec. Such a rate is higher than what typically exists during normal blood flow in a healthy human. This high rate (72 cm/sec) was selected for purposes of comparison in order to present a worst case detection scenario for the methods described herein.

FIG. 13 shows that three spatial frequency eigenvalue modes 1310 are excited with sufficient energy to exceed the 3 db ERB threshold for the 35 cm/sec flow velocity. In contrast, FIG. 14 indicates that only two spatial modes 1410 exceed the ERB threshold level at a notably small value of the estimated ERB. The discrimination provided by these two extreme cases illustrates the presence of detected turbulent flow induced noise.

Figure 15:
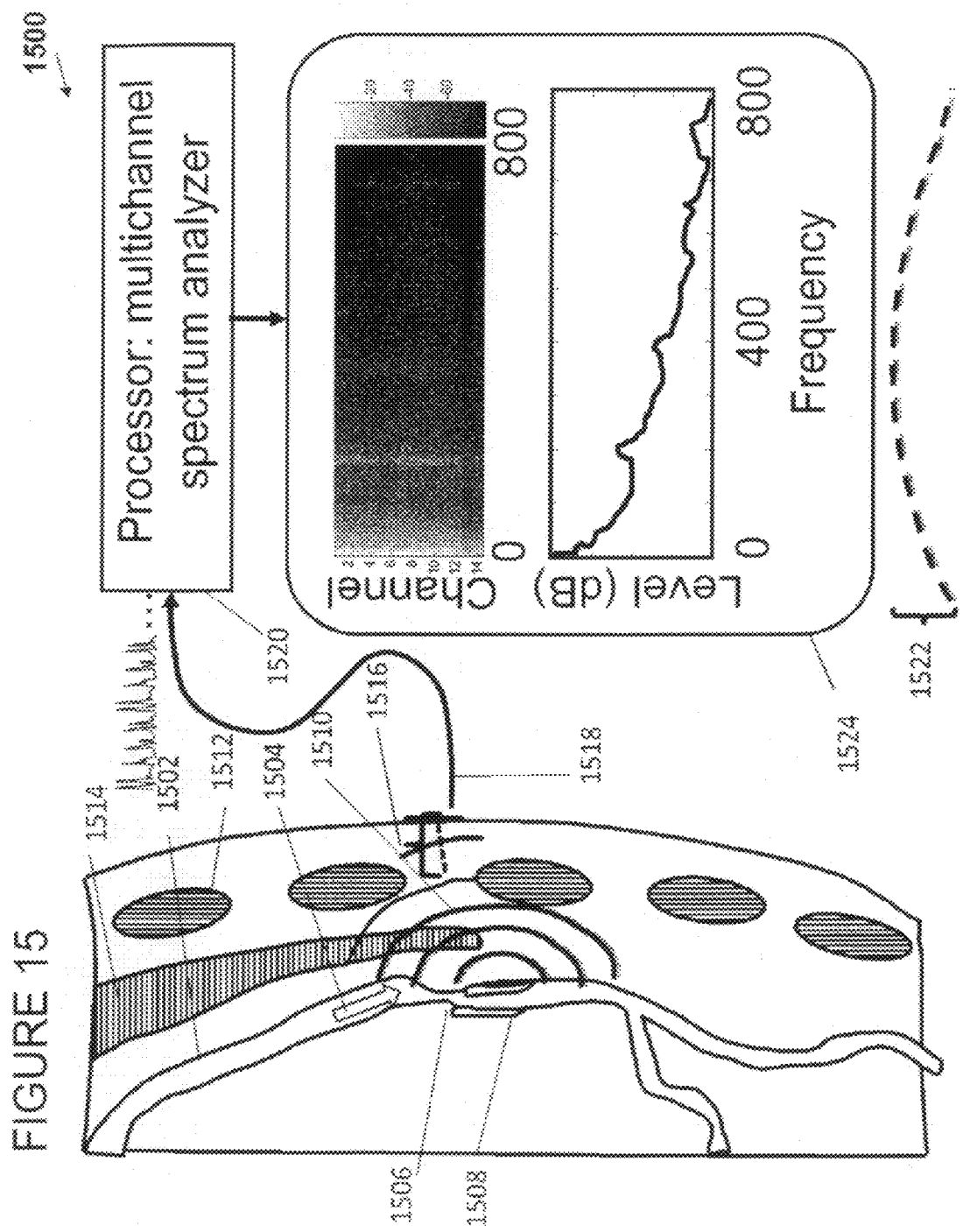
FIG. 15 illustrates an apparatus rendered in part with a grey scale image according to embodiments of the invention.

FIG. 15 illustrates, generally at 1500, an apparatus according to embodiments of the invention. With reference to FIG. 15 and as is similarly shown in FIG. 1A, a cross-sectional view of a human is presented. In FIG. 15, the cross section contains a coronary artery 1502. A direction of blood flow is indicated at 1504. An occlusion in the artery 1506 participates in causing downstream blood flow turbulence 1508. As described above in conjunction with FIG. 1A, blood flow turbulence produces a state of vibration 1510 in the human's body which propagates energy in the form of elastic waves 1510. The elastic waves produce vibration of the surface of the human and are measured non-invasively by one or more sensors 1516.

As the elastic wave energy 1510 propagates through the human's body it interacts with internal structures such as lung 1514 and ribs 1512. In various embodiments, it can be desirable to measure the vibration of the surface of the human in-between such ribs 1512, by placing a vibration transducer(s) in the intercostal space (between ribs) as shown by the placement of sensor 1516.

Depending on the geometry of the surface of the human, the surface may provide a curved surface, such as is indicated by 1522. The sensor or array of sensors is placed in such a manner as to conform to the geometry of the surface 1522.

A variety of types of transducers can be used to measure vibration of a surface of a human. For example, a film sensor such as described above in conjunction with FIG. 1A can be used as well as other sensors, such as for example a laser based sensor. Sensors that respond to displacement, velocity, and acceleration can be used to measure the vibrational energy that manifests on the surface of the human. In various embodiments, proximity sensors can be used. Sensors as of now yet unknown can be used to measure the vibration of the surface of the human. Embodiments of the invention are not limited by the choice of sensor used to non-invasively measure the vibrational energy manifest on the surface of the human. Those of skill in the art will note that if a laser based sensor is used, physical contact between the sensor and the surface of the human is not necessary as a laser can be used to measure the surface without making physical contact apart from the laser beam interacting with the surface.

The output of the sensor(s) is input at 1518 into a spectrum analyzer 1520. Spectrum analyzer 1520 is in various embodiments a single or multi-channel spectrum analyzer that performs a transformation from time to frequency. The resulting transformation has been referred to above in conjunction with FIG. 3 as a complex Fourier spectrum of the vibrational cardiac data and the ensemble average of the amplitude squared spectrum is referred to below as a vibrational frequency power spectrum estimate or simply "spectral estimate" or spectral estimates" when plural spectra are referred to. As used herein, in this description of embodiments and in the figures, it is understood by those of skill in the art that the terms power spectral density estimate (PSD), absolute (PSD) level, spectrum level, level, etc. refer to the amplitude of a power spectrum estimate. Furthermore, it is common in the art to express the level of a power spectrum as a decibel representation where the units are abbreviated as "dB." In various embodiments, the vibrational frequency power spectrum estimate is presented on a display 1524 for view by a doctor or technician or the vibrational frequency power spectrum estimate can be analyzed by an automated system to extract features related to a condition of health of a coronary artery. Such an automated system is configured in various embodiments as described above in conjunction with FIG. 1B.

As described below in the figures that follow, the vibrational frequency power spectrum estimate is used to quantify features and their characteristics which are used to support a diagnosis of a state of health of a human. A list of features and their characteristics includes, but is not limited to blood flow turbulence energy from: (a) ventricular refilling turbulence characterized by a low frequency (LF) plateau with feature characteristics of level, width, and roll-off rate (slope) from the LF plateau; (b) arterial blood flow turbulence induced by diffuse occlusions characterized by a characteristic that captures the broadband spectrum level increase in the high frequency (HF) band above a 200 to 400 Hz roll-off band relative to the LF plateau level; (c) relatively localized occlusions described as having a band of surface curvature radials that induce spectral energy swaths characterized to first order by the characteristics of spectrum level, center frequency, and bandwidth; (d) localized occlusions with a dominant surface curvature that induces spectrally narrow whistles characterized by the characteristics of level (amplitude) and center frequency; (e) a roll-off over a band of frequency that can occur anywhere in a frequency spectrum; and (f) a user defined feature. One or more features or multiples of a single type of feature can be evident in the vibrational frequency power spectrum estimates obtained from humans. As used in this description of embodiments, when reference is made to a feature, the characteristics (shape) of the feature are also implied thereby.

Figure 16:
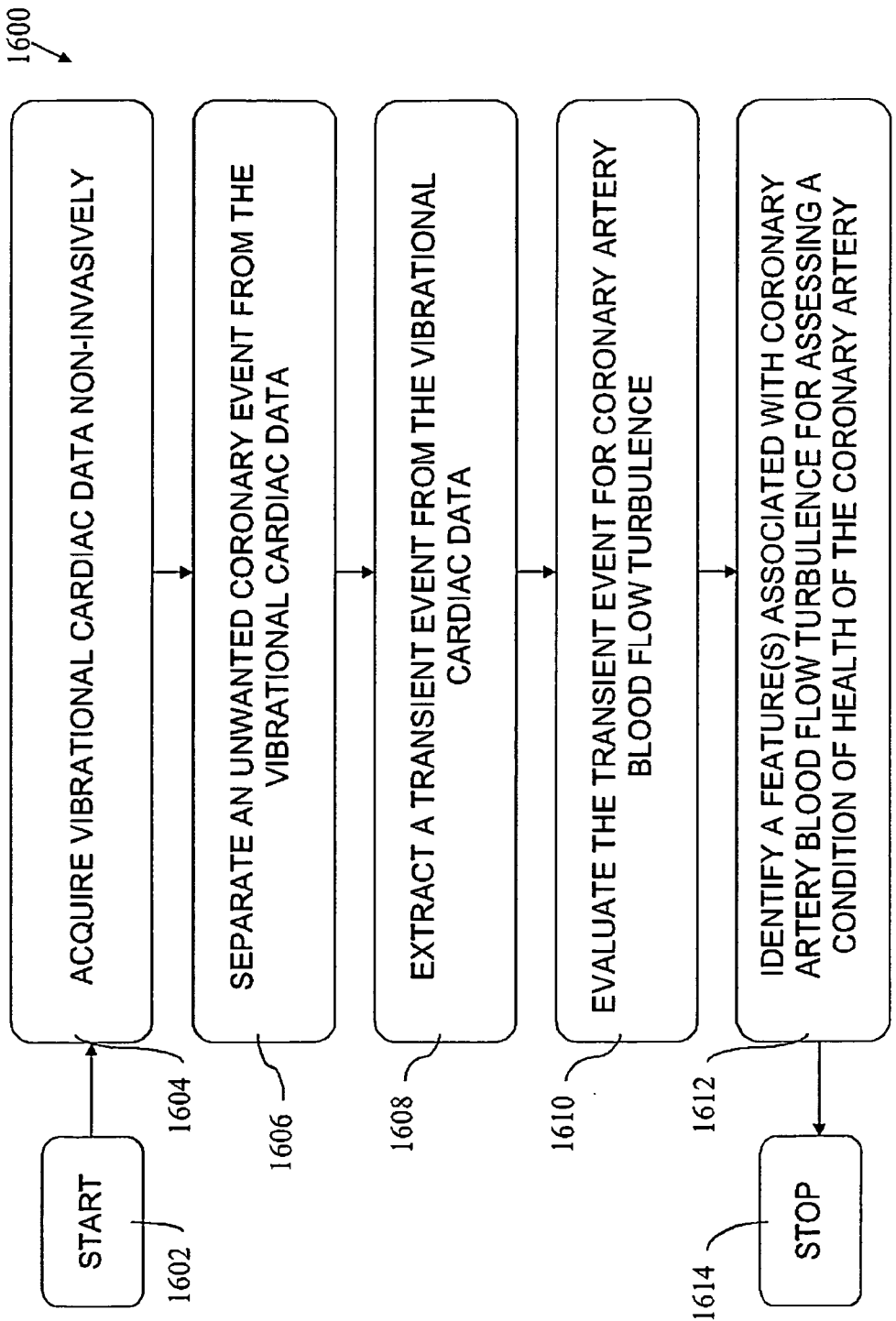
FIG. 16 illustrates a method to obtain vibrational cardiac data according embodiments of the invention.

FIG. 16 illustrates, generally at 1600, a method to assess a condition of health of a coronary artery using vibrational cardiac data, according to embodiments of the invention. With reference to FIG. 16, a method starts at a block 1602. At a block 1604 vibrational cardiac data is acquired non-invasively from a surface of a human. At a block 1606 unwanted coronary events are separated from the vibrational cardiac data. Separating unwanted coronary events such as heart valve vibrations are described above in conjunction with FIG. 3. At a block 1608 a transient event is extracted from the vibrational cardiac data. The transient event is associated with blood flow turbulence and is used to assess a condition of health of a coronary artery. At a block 1610 the transient event is evaluated for an indication of energy due to coronary artery blood flow turbulence and the corresponding state of health of the coronary artery. At a block 1612 a feature is identified in the vibrational frequency power spectrum estimate that is associated with blood flow turbulence. Relating the feature(s), or characteristic(s) thereof in the vibrational frequency power spectrum estimate to a state of health in the coronary arteries of a human is described below in conjunction with the figures that follow. At a block 1614 the method stops.

Figure 17:
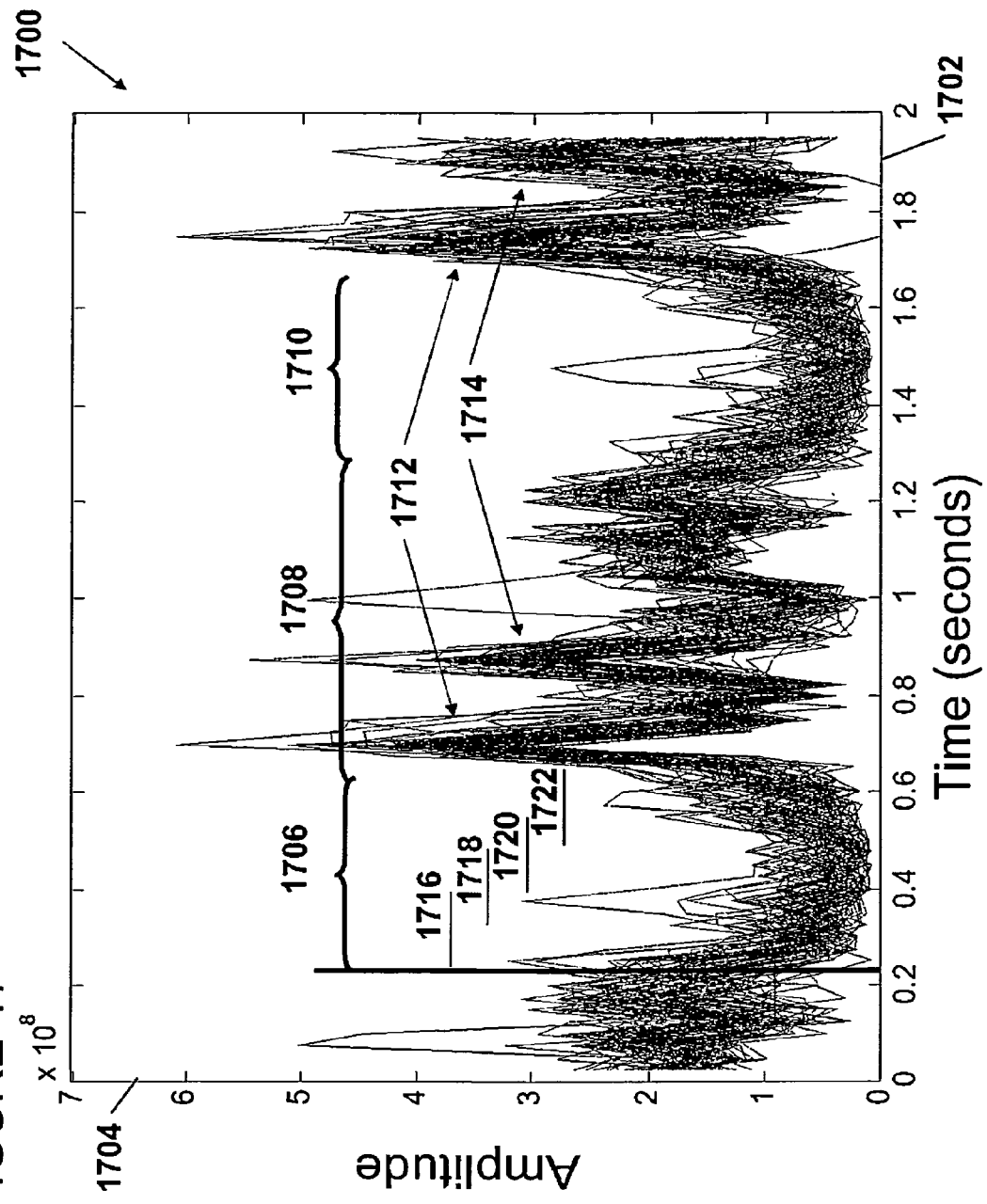
FIG. 17 illustrates time series plots of vibrational cardiac data, according to embodiments of the invention.

FIG. 17 illustrates, generally at 1700, time series plots of synchronized vibrational cardiac data, according to embodiments of the invention. With reference to FIG. 17, time is plotted on a horizontal axis 1702 and amplitude is plotted on a vertical axis 1704. As described above in conjunction with FIG. 3, vibrational cardiac data was collected non-invasively from a surface of human with a transducer. Displayed in FIG. 17 is a stack of 67 synchronized heart-cycle time series waveforms. The stack of 67 heart-cycle time series waveforms is from one channel of a 14 channel array. In order to maximize signal-to-noise ratio (SNR) in a given measurement, heart cycles can be pruned, thereby discarding outliers that are contaminated with various sources of noise. As described above, various extraneous stimuli in the environment can manifest themselves as noise in vibrational cardiac data. These stimuli include, but are not limited to, stomach gurgling, etc. The inter-waveform correlation coefficient with a master replica exceeds 0.87 for all of the 67 waveform pairs in FIG. 17.

Similar to the representation of heart-cycle waveforms shown above in FIG. 2 or FIG. 7, two diastolic intervals are shown in FIG. 17. A first diastolic interval is observed at 1706. The first diastolic interval 1706 is followed by a systolic interval 1708 and then a second diastolic interval 1710. A first heart sound is indicated at 1712 and a second heart sound is indicated at 1714. Heart sounds 1712 and 1714 are some of the unwanted coronary events that are separated from the vibrational cardiac data. During diastole, blood flow in the coronary arteries is at a maximum and the unwanted heart sound vibrations are at a minimum. Therefore, the vibrational cardiac data that occurs during a diastolic interval are processed to assess a condition of health of the coronary arteries. Blood flow through the coronary arteries is at a maximum at the onset of diastole and then decreases as a function of time through diastole. Thus, information about blood flow turbulence and a corresponding state of health of a human's coronary artery can be obtained from an analysis of the blood flow turbulence energy that occurs during diastole.

In one or more embodiments, a diastolic interval (window), such as 1706, is divided into a plurality of time slots, such as the example of four time slots shown in FIG. 17 as indicated by 1716, 1718, 1720, and 1722. Transforming the time series waveforms that occur in these time slots to the frequency domain produces vibrational frequency power spectra estimates which are compared in order to obtain information about both the transient and stationary behavior of the blood flow turbulence.

As described above in conjunction with FIG. 3 through FIG. 7, a time slot is an interval of time with a known start time and duration time relative to an established time mark. A time slot is also referred to herein as a sub-interval or a portion of a diastolic interval. Note also that a time slot can be configured to be equivalent in duration to a diastolic interval. The time mark can be selected either manually or automatically by the system. In one embodiment, a preferred location for a start time is very early diastole during the rapid early ventricular filling phase, when coronary blood flow is at a maximum rate. In one embodiment, a typical time slot length can be in the range 0.125 to 0.1825 seconds in duration when four (4) time slots are used to process the diastolic window with 50% overlap between time slots. Other amounts of time slot overlap can be used and in some embodiments time slots can be configured without overlap. The example of four (4) time slots with a 50% overlap is provided merely for illustration and does not present any limitation to embodiments of the invention. Throughout diastole, the cross-sectional shape of the coronary artery is changing and the frequency content of the blood flow turbulence induced energy is changing. These changes are observed in the vibrational frequency power spectra estimates discussed in conjunction with the figures below.

Figure 18:
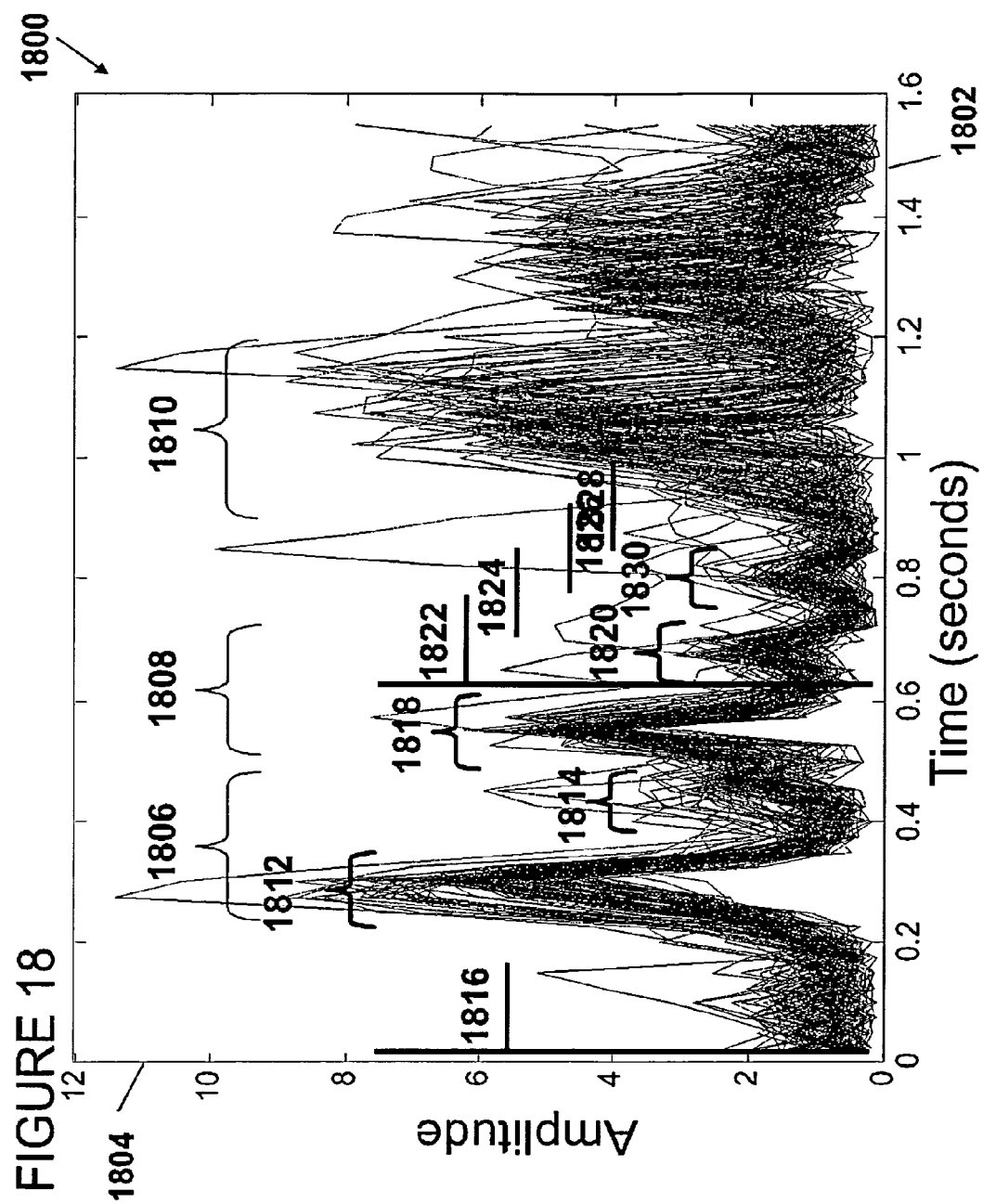
FIG. 18 illustrates another set of time series plots of vibrational cardiac data collected from a human whose coronary arteries are in a healthy condition, according to embodiments of the invention.

FIG. 18 illustrates, generally at 1800, another set of time series plots of vibrational cardiac data collected from a human whose coronary arteries are in a healthy condition, according to embodiments of the invention. With reference to FIG. 18, a stack of 109 synchronized heart-cycle waveforms are displayed in the figure with time plotted on an axis 1802 and amplitude plotted on an axis 1804. The correlation coefficient computed between a master replica and all other heart cycles exceeded 0.89 for pairs of heart cycles in the stack of FIG. 18. The human corresponding to the data shown in FIG. 18 is a forty three (43) year old male who is symptom free with respect to cardiovascular disease. The individual exercises regularly and has a total cholesterol value of 170. The vibrational cardiac data from this individual is used below to provide information on blood flow turbulence from a healthy state of coronary artery health.

The first heart sound interval is indicated at 1806. The first heart sound interval 1806 includes a closure snap 1812 of a mitral valve and a closure snap of a tricuspid valve at 1814. The second heart sound interval 1808 includes an aortic valve closure 1818 and 1820. 1820 is either a pulmonary valve closure and/or an early ventricular refilling turbulence transient. As described above, the diastolic interval is the region of interest. The aforementioned heart sounds constitute unwanted coronary events and are eliminated from the processing by placement of the time slots. The time intervals that are used for estimation of the vibrational frequency power spectra are pre first heart sound time slot 1816, diastolic interval time slot 1 (1822), diastolic interval time slot 2 (1824), diastolic interval time slot 3 (1826), diastolic interval time slot 4 (1828). A heart sound referred to as the fourth heart sound is indicated at 1830, which is caused by diastole refilling turbulence transient.

The stack of one hundred and nine (109) vibrational cardiac data measurements from FIG. 18 are transformed to the frequency domain using techniques such as the Fast Fourier Transform (FFT). Other techniques can be used to transform to the frequency domain, the FFT is used for example and does not limit embodiments of the invention.

Figure 19:
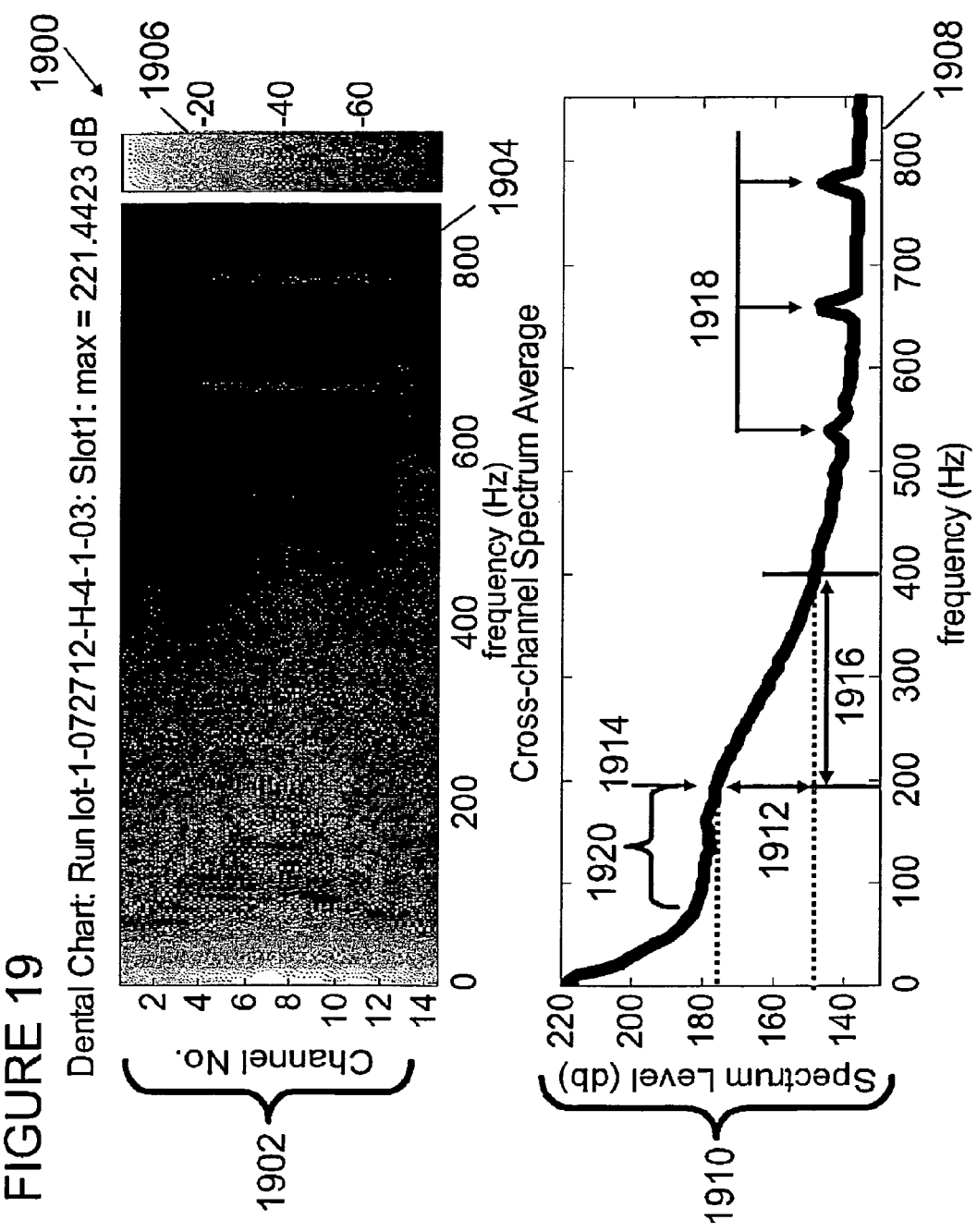
FIG. 19 illustrates vibrational frequency power spectra estimates corresponding to a time slot 1816 shown in FIG. 18, rendered in part with a grey scale image according to embodiments of the invention.

FIG. 19 illustrates, generally at 1900, vibrational frequency power spectra estimates corresponding to a time slot 1816 shown in FIG. 18, according to embodiments of the invention. With reference to FIG. 19, the one hundred and nine (109) time slot 1 sub-intervals in the synchronized heart cycles are Fourier transformed and then the amplitude squared of the complex Fourier transforms are ensemble averaged for a given channel. In one embodiment, the procedure is repeated for each channel when an array of transducers is used to obtain the vibrational cardiac data. The averaged vibrational frequency power spectrum estimate for each channel is indicated for a channel number at 1902 and is plotted as a function of frequency on an axis 1904. The corresponding normalized amplitude is indicated by grey scale with amplitude reference given at 1906 in decibels.

The lower plot in FIG. 19 displays the vibrational frequency power spectrum estimate obtained by averaging a subset of channels from 1902. In this case, channels one (1) through thirteen (13) from the fourteen (14) channel array are averaged together. Frequency is indicated on a horizontal axis at 1908. Spectrum level is indicated on a vertical axis at 1910.

The dominant feature of the spectral estimates is a low frequency plateau 1920. The low frequency plateau 1920 includes a relatively flat low frequency region of the spectrum between approximately eighty (80) and two hundred (200) cycles per second (Hz). Above 200 Hz the spectrum rolls-off decreasing at a rate of 27 to 29 decibels/octave in the 200 to 400 Hz octave. A decrease of 27 to 29 decibels is indicated at 1912 and the 200 to 400 Hz octave is indicated at 1916. This plateau, in the 80 to 200 Hz band coincides with atrioventricular valve blood flow turbulence during ventricular refilling. The level and width of this plateau is proportional to a valve flow rate and therefore to flow velocity. Mechanisms for the generation of this low frequency flow energy is a combination of valve vibration induced by blood flow shedding from the valve flaps and valve jet flow induced pressure waves in the ventricles propagating to and exiting the ventricle heart wall. The valve vibrational energy propagates by means of elastic waves in the walls of the heart chamber. If there is other energy that is time coincident with the third and fourth heart sounds, e.g., 1820 and 1830 (FIG. 18), then the corresponding spectrum is masked by 1820 and 1830 (FIG. 18). Power line artifacts of 60 Hz are indicated at 1918.

Figure 20:
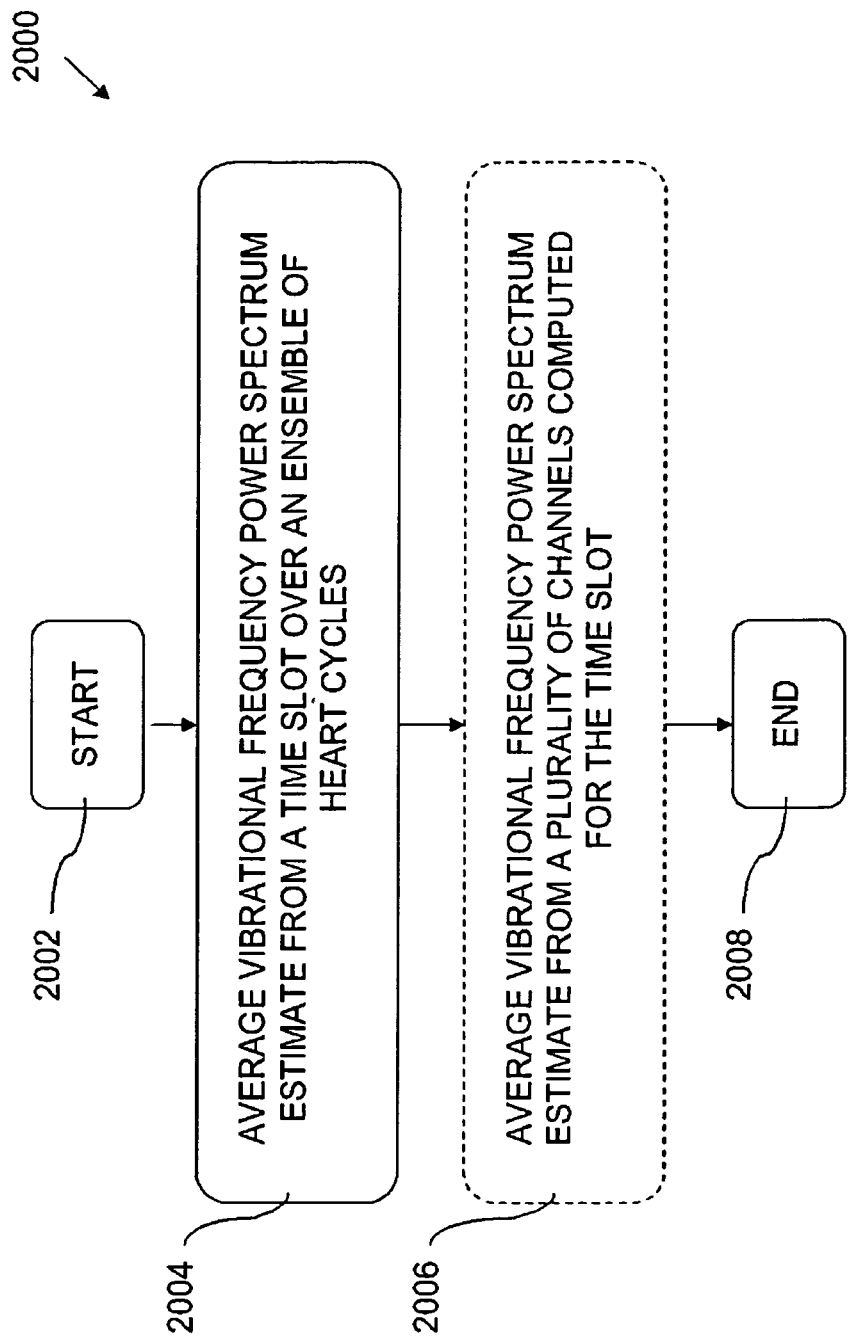
FIG. 20 illustrates a method for averaging vibrational frequency cardiac data, according to embodiments of the invention.

FIG. 20 illustrates, generally at 2000, a method for averaging vibrational frequency cardiac data, according to embodiments of the invention. With reference to FIG. 20, a method starts at a block 2002. At a block 2004, in one embodiment as described above in conjunction with FIG. 19, an ensemble of vibrational frequency power spectra estimates, corresponding to time slots in the synchronized heart cycles are averaged. Optionally at a block 2006, for each channel of an array, the resulting plurality of time averaged vibrational frequency power spectra estimates are averaged together. In one embodiment, an example of such averaging in time and transducer channel position space is shown in FIG. 19 at 1910. The process stops at a block 2008. Note that averaging vibrational frequency power spectra estimates can be performed on all or a subset of channels.

Figure 21:
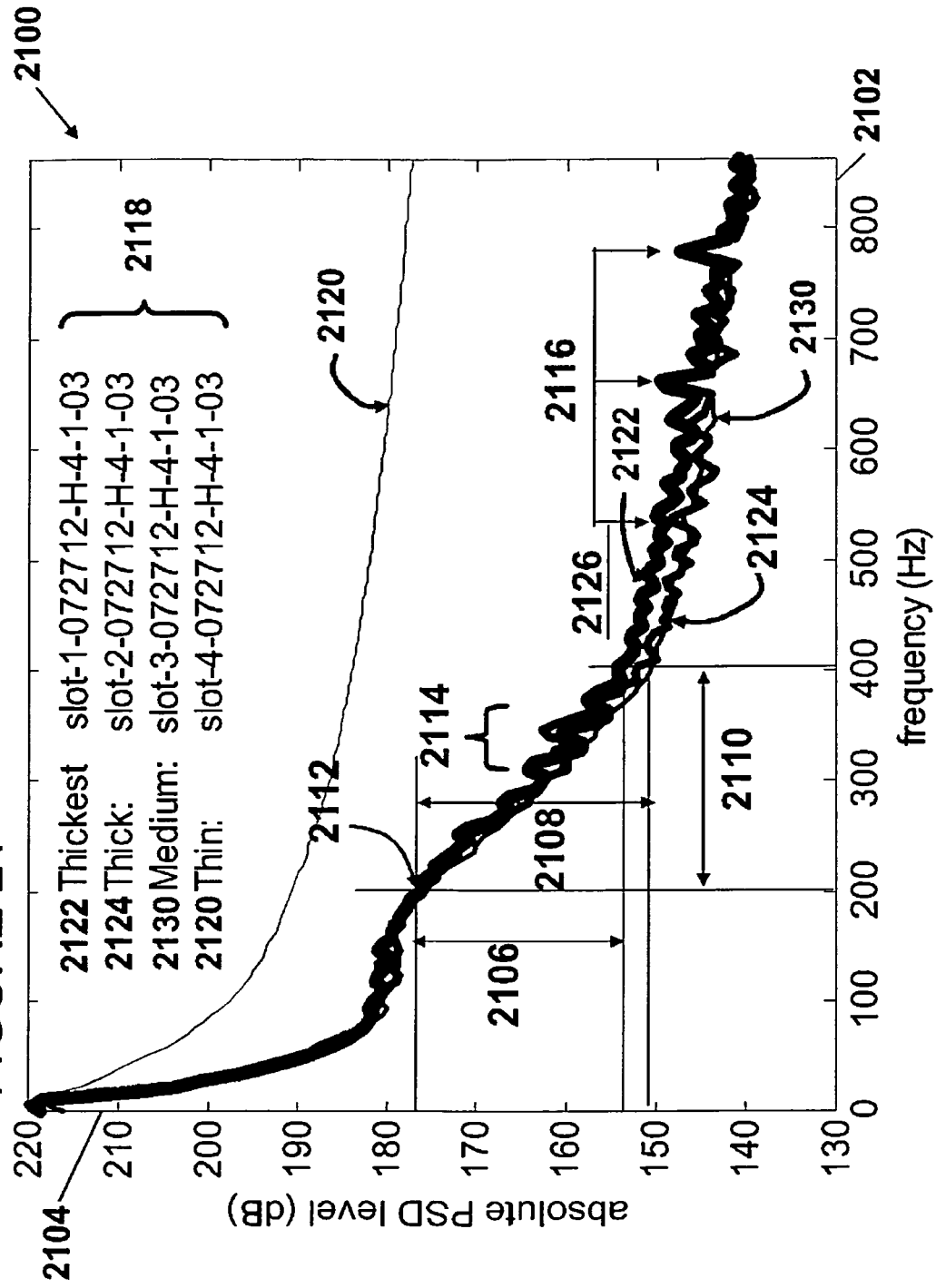
FIG. 21 illustrates an overlay of space-time averaged vibrational frequency power spectra estimates corresponding to data from FIG. 18, according to embodiments of the invention.

FIG. 21 illustrates, generally at 2100, an overlay of space-time averaged vibrational frequency power spectra estimates corresponding to data from FIG. 18, according to embodiments of the invention. With reference to FIG. 21, the space-time averaged vibrational frequency power spectrum estimates 2118 are plotted with frequency on an axis 2102 and spectrum level on an axis 2104. A twenty five (25) dB roll-off, indicated at 2106, occurs in the 200-400 Hz band indicated at 2110 for the averaged power spectrum estimate for time slot 2, indicated at 2124. A 28 dB roll-off, indicated at 2108, occurs in the 200-400 Hz band 2110 for the averaged power spectrum estimate for time slot 1, indicated at 2122. Reference point 2112 is the 3 dB down point from the low frequency plateau. Reference point 2112 is used to measure the roll-offs described directly above. Artifacts of 60 Hz power line harmonics are evident at 2116. Those of skill in the art will recognize that such narrow band 60 cycle artifacts are tolerable as long as they do not bias the estimated power spectral density (PSD) level outside of their narrow band.

Note that the spectrum roll-off of time slot 1 2122 in a band of frequency above 400 Hz is different between FIG. 19 (pre mitral valve closure time slot) and the roll-off shown in FIG. 21. The spectrum rolls-off more slowly in the band of frequency above 400 Hz in FIG. 21 because in FIG. 18 the time slot 4 interval captures the leading edge of the next mitral valve closure snap, which contributed to a very broad band of energy at higher frequencies. The spectrum level increase above 400 Hz continues in frequency and is completely dominated by broad band energy at 2120. Valve closure snaps result in significant energy and elevated levels as can be seen by 2120 which corresponds to capturing only a portion of the energy in the mitral valve closure snap by time slot 4 (1828 in FIG. 18). Thus, by eliminating unwanted cardiac events such as heart valve open or close motions the energy that is due to blood flow turbulence can be detected by the procedure.

With reference to FIG. 21, the spectrum for time slot 1 2122 could contain energy from the pulmonary valve closure 1820 (FIG. 18) and the early ventricle refilling 1830 (FIG. 18). The pulmonary valve snap will generate broadband energy above 200 Hz which appears to be at a very low level because this band has the lowest spectrum level for all four time slots 2118. The ventricle refilling will produce energy below 200 Hz because it results from the flow over the surface of the atrioventricular valves which have relatively large surfaces of order centimeters with low curvatures relative to the inner dimensions of a coronary artery, which has dimensions of order millimeters with proportional curvatures.

The averaged spectrum level for time slot 2 is indicated at 2124. Time slot 2 captures the trailing edge of ventricle refilling (S3), the leading edge of S4 and a quiet area which permits measurement of energy due to blood flow turbulence in the left coronary artery. A moderate strength spread spectrum energy swath is indicated at 2114. This swath has a center frequency of 350 Hz, a bandwidth of approximately 60 Hz, and a signal-to-noise ratio (SNR) of approximately 8-10 dB. This measurement indicates that energy generated from blood flow turbulence is present in symptom free humans with respect to coronary artery disease.

Time slot 2, shown at 2124, also indicates a low level of spectrum ripple. The ripple has a period of approximately 30 to 40 Hz and a peak-to-valley amplitude differential of 2 to 3 dB as indicated at 2126. This effect is consistent with an interference pattern produced by energy propagating from a vibration source to a vibration transducer (measurement location) along more than a single path. Phase coherent energy arrivals on different paths can periodically suppress or support each other and a frequency spectrum ripple period of 30 to 40 Hz is consistent with elastic wave propagation speeds in tissue with multiple path length differences on the order of centimeters.

FIG. 22 illustrates, generally at 2200, a set of time series plots of vibrational cardiac data collected from a clinically diagnosed individual with a history of coronary artery disease, according to embodiments of the invention. With reference to FIG. 22, the subject of the measurements presented in FIG. 22 is a male in his late sixties. Six months prior to the measurement, this man was diagnosed with total blockage of Left Anterior Descending (LAD) coronary artery and underwent a stent procedure that restored full LAD flow. Presented in FIG. 22 are one hundred and four (104) synchronized heart cycle waveforms of vibrational cardiac data. These data have been collected as previously described and, in this embodiment, an array of fourteen (14) transducers was used to collect the vibrational cardiac data. The synchronized heart cycle waveforms exhibit a master replica pair wise correlation coefficient greater than 0.91.

In FIG. 22 time is plotted on an axis 2202 and amplitude is plotted on an axis 2204. A systolic interval is indicated at 2206 and a diastolic interval is indicated at 2208. In this embodiment, the diastolic interval 2208 has been partitioned into four (4) overlapping time slots 2210, 2212, 214, and 2216. Transformations from time to frequency are performed on each heart cycle waveform within each time slot. This process is repeated for each channel of the array of fourteen transducers.

In one embodiment, for each channel, an ensemble of power spectrum estimates are then averaged for the same time slot in each heart cycle. The results of the averaged time slot power spectrum estimates (time to frequency transformations) are shown in FIG. 23 on a channel-by-channel basis with the time ensemble average at the top and as a channel average across the array at the bottom.

Figure 23:
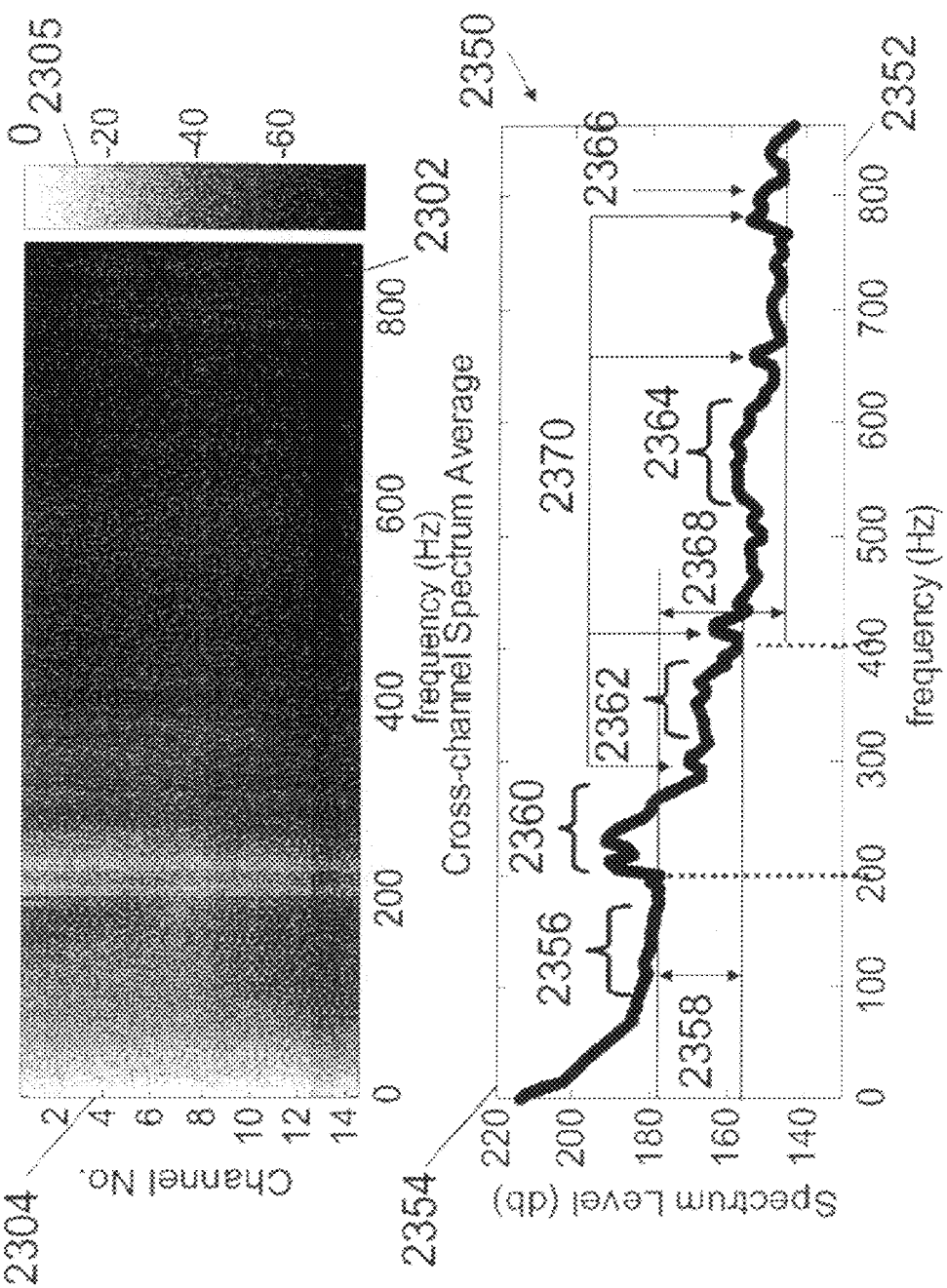
FIG. 23 illustrates a set of vibrational frequency power spectra estimates corresponding to the time series from FIG.

FIG. 23 illustrates, generally at 2300, a set of vibrational frequency power spectra estimates corresponding to the time series from FIG. 22, according to embodiments of the invention. With reference to FIG. 23, each of the averaged spectral estimates for each channel are displayed at 2300 with frequency on an axis at 2302, channel number on an axis 2304 and normalized spectrum level is indicated at 2305 as gray scale. Thirteen of the fourteen time averaged channel spectrum estimates from 2300 are averaged together and plotted in 2350 with frequency on an axis at 2352 and spectrum level on an axis 2354. Averaging as was done in both time (ensemble of heart cycles) and space (across channels) improves a signal-to-noise ratio of the measurement. Such averaging is not always required and in some embodiments with sufficient signal-to-noise ration (SNR), meaningful information is obtained from a single time to frequency transformation of a single heart cycle from one transducer.

The processed vibrational frequency power spectrum estimate plotted in FIG. 23 at 2350, corresponds to the first time slot 2210 (FIG. 22) in the diastolic interval 2208 (FIG. 22). Features are present in 2350 that are used to identify coronary artery blood flow turbulence. One feature is a low frequency plateau, which exists between approximately 80 and 150 Hz and is indicated at 2356. This low frequency plateau is associated with valve flow as previously discussed. Another feature is a low frequency roll-off from the plateau which occurs between 80 and 150 Hz. The roll-off of the amplitude is 18 dB as indicated at 2358 over the 200 to 400 Hz frequency octave. Another feature is a strong spread spectrum energy swath which occurs at 2360. This strong swath is characterized by a center frequency of 230 Hz, a bandwidth of 80 Hz, and a signal-to-noise ratio of 18 dB. Yet another feature is a weak spread spectrum energy swath which occurs at 2362. This weak swath is characterized by a center frequency of 365 Hz, a bandwidth of 55 Hz, and a signal-to-noise ratio of 7 dB.

Another feature is a medium spread spectrum energy swath which occurs at 2364. This medium swath is characterized by a center frequency of 570 Hz, a bandwidth of 100 Hz, and a signal-to-noise ratio of 8 dB. Another feature is a frequency band-limited whistle at 2366. Whistle 2366 is characterized by a center frequency of 805 Hz and amplitude of 8 dB. Another feature is a difference in amplitude between the low frequency plateau 2356 and a high frequency broad band level. This difference is approximately 30 dB as indicated at 2368. Several power line artifacts of 60 Hz are evident at 2370. These power line artifacts are not considered to be features.

FIG. 24 illustrates, generally at 2400, an overlay of vibrational frequency power spectra estimates from multiple slots corresponding to the human's data shown in FIG. 22, according to embodiments of the invention. With reference to FIG. 24, time and channel averaged vibrational frequency power spectrum estimates for each time slot (2210, 2212, 2214, and 2216 from FIG. 22) are plotted on a graph with frequency on an axis 2402 and spectrum level on an axis 2404. Time slot 1, time slot 2, and time slot 3 contain features, the types of which were described above, which are associated with coronary artery blood flow turbulence and a state of health of a coronary artery. Time slot 4 (2216 in FIG. 22) contains valve snap energy and has been placed to capture part of the valve snap to illustrate the fact that the first three time slots (2210, 2212, and 2214 from FIG. 22) are measuring blood flow turbulence.

Notably, the characteristics of some of the features exhibit transient behavior and have changed between time slot 1 and time slot 2. Similarly, characteristics of features have also changed between time slot 1 and time slot 3 and between slot 2 and slot 3. For example, a feature in time slot 1 is a strong spread spectrum swath 2406. This strong spread spectrum swath 2406 has a center frequency of approximately 230 Hz and a bandwidth of approximately 90 Hz 2407. In time slot 2 (2212) the strong spread spectrum swath 2406 (from time slot 1 2210) has transformed into a frequency band limited whistle at 2408 with a center frequency of 200 Hz at 2424. Another example of a feature changing between time slots is medium spread spectrum energy swath 2412 in time slot 2 (2212) transforming into a frequency band limited whistle 2414 in time slot 3 (2214). The estimated center frequency of the swath 2412 and the whistle 2414 is 390 Hz as indicated at 2422.

Extraction of features, from such an individual and comparison of the characteristics of the features between time slots permits identification of a state of health of the individual's coronary artery or arteries. Changes in characteristics of a feature(s) from one time slot to another within a given human's vibrational cardiac data permits identification of a state of health of coronary arteries. Here, note that in FIG. 22 the clinically diagnosed individual, who underwent the stent procedure, has turbulence inducing occluded arteries and a features which exhibit transient behavior between at least two time slots. By comparing the features that exist in each time slot a transient event can be identified and extracted and a determination can be made with respect to a state of health of the associated coronary artery(s) regarding the presence of arterial blockage.

FIG. 25 illustrates, generally at 2500, a method for identifying a feature related to coronary artery blood flow turbulence using a single human, according to embodiments of the invention. With reference to FIG. 25, a process starts at a block 2502. At a block 2504, a diastolic interval of a heart cycle is partitioned into at least two time slots. At a block 2506 a time to frequency transformation is performed on vibrational cardiac data collected from the time slots created in the block 2504. At a block 2508 one or more features and/or characteristics of the features that are associated with a transient event from blood flow turbulence in a coronary artery are identified. These transient events are then analyzed to determine a state of health of the human. A process stops at a block 2510. In one or more embodiments, a monitoring paradigm for heart disease includes periodic measurements made on an individual. Comparison of the individual's measurements over time will indicate an increase in blood flow turbulence energy if the individuals state of coronary artery health declines. Such comparison can be performed with the individual's own data, as described above in conjunction with FIG. 25, or in other embodiments; comparison can be made with blood flow turbulence measurements made from known clinically diagnosed states, as described below.

FIG. 26 illustrates, generally at 2600, a comparison of vibrational cardiac data from multiple humans, according to embodiments of the invention. With reference to FIG. 26, frequency is plotted on an axis at 2602 and spectrum level is plotted on an axis at 2604. The vibrational cardiac data plotted in FIG. 26 are the time and channel averaged vibrational frequency power spectrum estimates for time slot 1 (for the symptom free person at 2630) data previously shown in FIG. 21 and the person whose coronary arteries indicate coronary artery turbulence at 2620, which are data previously shown in FIG. 23 and FIG. 24 (2210) for the clinically diagnosed individual.

The low frequency plateau was previously described for 2630 in FIG. 19 as extending from 90 to 180 Hz. The location of the strong spread spectrum energy swath 2606 slightly obscures the high frequency end of the low frequency plateau; however the low frequency plateau for both 2620 and 2630 are substantially equivalent in amplitude.

The roll-off of the low frequency plateau differs between the symptom free person's measurement 2620 and the clinically diagnosed person's measurement 2630. For 2630 the roll-off is 24 dB indicated at 2612. For 2620 the roll-off is 17 dB indicated at 2614.

The spread spectrum energy swath bandwidths are 90 Hz for 2606, 110 Hz for 2608, and 110 Hz for 2610. Spread spectrum energy swath 2606 has a center frequency of 230 Hz at 2616; spread spectrum energy swath 2610 has a center frequency of 570 Hz at 2618. The signal-to-noise ratio for spread spectrum swath 2606 is 19 dB and the spread spectrum swath 2610 has a signal-to-noise ratio of 9 dB.

FIG. 27 illustrates, generally at 2700, a method for identifying a feature related to coronary artery blood flow turbulence using multiple humans, according to embodiments of the invention. With reference to FIG. 27, a process starts at a block 2702. At a block 2704 a time to frequency transformation is performed on vibrational cardiac data collected during a diastolic interval of a heart cycle, thereby resulting in a vibrational frequency power spectrum estimate. At a block 2706 a feature(s) is extracted from the vibrational frequency power spectrum estimate with the aid of previously identified and clinically verified features that are related to blood flow turbulence in a coronary artery and the related condition of health of the coronary artery.

Following the teaching presented in the figures above, in various embodiments, process block 2706 includes a plurality of measurements, which can be referred to as a library of measurements. The library of measurements thus created contains different features (with their associated characteristics) of blood flow turbulence in the frequency domain that are associated with different conditions of health of coronary arteries in clinically verified cases. These features are also referred to as "signatures" of blood flow turbulence and the associated pathology. Note that blood flow turbulence is not always associated with a diseased condition. At times, a measure of blood flow turbulence indicates a healthy condition (refer to FIG. 19 and FIG. 21). Note that in different embodiments, databases of library measurements can be assembled in different ways according to the teachings presented herein. For example, a database can be based on transients that occur during diastole. A database(s) can be assembled based on symptom free individuals, thereby establishing a plurality of measurements of healthy conditions. A database(s) can be assembled that is based on features and their characteristics that are associated with clinically verified known pathologies, i.e., degree of blockage of an artery's cross-section, presence of a stent or lack thereof, etc. Databases can be combined to form databases that combine self-evaluation changes in spectral content from one time slot to another time slot within a diastolic interval along with comparison measurements from data collected on a population of humans. Thus, apparatuses and methods have been described which permit a condition of health of a human's coronary artery(s) to be evaluated non-invasively.

For purposes of discussing and understanding the embodiments of the invention, it is to be understood that various terms are used by those knowledgeable in the art to describe techniques and approaches. Furthermore, in the description, for purposes of explanation, numerous specific details are set forth in order to provide a thorough understanding of the present invention. It will be evident, however, to one of ordinary skill in the art that the present invention may be practiced without these specific details. In some instances, well-known structures and devices are shown in block diagram form, rather than in detail, in order to avoid obscuring the present invention. These embodiments are described in sufficient detail to enable those of ordinary skill in the art to practice the invention, and it is to be understood that other embodiments may be utilized and that logical, mechanical, electrical, and other changes may be made without departing from the scope of the present invention.

Some portions of the description may be presented in terms of algorithms and symbolic representations of operations on, for example, data bits within a computer memory. These algorithmic descriptions and representations are the means used by those of ordinary skill in the data processing arts to most effectively convey the substance of their work to others of ordinary skill in the art. An algorithm is here, and generally, conceived to be a self-consistent sequence of acts leading to a desired result. The acts are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, waveforms, data, time series or the like.

It should be borne in mind, however, that all of these and similar terms are to be associated with the appropriate physical quantities and are merely convenient labels applied to these quantities. Unless specifically stated otherwise as apparent from the discussion, it is appreciated that throughout the description, discussions utilizing terms such as "processing" or "computing" or "calculating" or "determining" or "displaying" or the like, can refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

An apparatus for performing the operations herein can implement the present invention. This apparatus may be specially constructed for the required purposes, or it may comprise a general-purpose computer, selectively activated or reconfigured by a computer program stored in the computer. Such a computer program may be stored in a computer readable storage medium, such as, but not limited to, any type of disk including floppy disks, hard disks, optical disks, compact disk read-only memories (CD-ROMs), and magnetic-optical disks, read-only memories (ROMs), random access memories (RAMS), electrically programmable read-only memories (EPROM)s, electrically erasable programmable read-only memories (EEPROMs), FLASH memories, magnetic or optical cards, etc., or any type of media suitable for storing electronic instructions either local to the computer or remote to the computer.

The algorithms and displays presented herein are not inherently related to any particular computer or other apparatus. Various general-purpose systems may be used with programs in accordance with the teachings herein, or it may prove convenient to construct more specialized apparatus to perform the required method. For example, any of the methods according to the present invention can be implemented in hard-wired circuitry, by programming a general-purpose processor, or by any combination of hardware and software. One of ordinary skill in the art will immediately appreciate that the invention can be practiced with computer system configurations other than those described, including hand-held devices, multiprocessor systems, microprocessor-based or programmable consumer electronics, digital signal processing (DSP) devices, network PCs, minicomputers, mainframe computers, and the like. The invention can also be practiced in distributed computing environments where tasks are performed by remote processing devices that are linked through a communications network.

The methods of the invention may be implemented using computer software. If written in a programming language conforming to a recognized standard, sequences of instructions designed to implement the methods can be compiled for execution on a variety of hardware platforms and for interface to a variety of operating systems. In addition, the present invention is not described with reference to any particular programming language. It will be appreciated that a variety of programming languages may be used to implement the teachings of the invention as described herein. Furthermore, it is common in the art to speak of software, in one form or another (e.g., program, procedure, application, driver, . . . ), as taking an action or causing a result. Such expressions are merely a shorthand way of saying that execution of the software by a computer causes the processor of the computer to perform an action or produce a result.

It is to be understood that various terms and techniques are used by those knowledgeable in the art to describe communications, protocols, applications, implementations, mechanisms, etc. One such technique is the description of an implementation of a technique in terms of an algorithm or mathematical expression. That is, while the technique may be, for example, implemented as executing code on a computer, the expression of that technique may be more aptly and succinctly conveyed and communicated as a formula, algorithm, mathematical expression, flow diagram or flow chart. Thus, one of ordinary skill in the art would recognize a block denoting A+B=C as an additive function whose implementation in hardware and/or software would take two inputs (A and B) and produce a summation output (C). Thus, the use of formula, algorithm, or mathematical expression as descriptions is to be understood as having a physical embodiment in at least hardware and/or software (such as a computer system in which the techniques of the present invention may be practiced as well as implemented as an embodiment).

A machine-readable medium is understood to include any mechanism for storing or transmitting information in a form readable by a machine (e.g., a computer). For example, a machine-readable medium includes read only memory (ROM); random access memory (RAM); magnetic disk storage media; optical storage media, flash memory devices; electrical, optical, acoustical or other form of non-transitory propagated signals (e.g., carrier waves, infrared signals, digital signals, etc.); etc.

As used in this description, "one embodiment" or "an embodiment" or similar phrases means that the feature(s) being described are included in at least one embodiment of the invention. References to "one embodiment" in this description do not necessarily refer to the same embodiment; however, neither are such embodiments mutually exclusive. Nor does "one embodiment" imply that there is but a single embodiment of the invention. For example, a feature, structure, act, etc. described in "one embodiment" may also be included in other embodiments. Thus, the invention may include a variety of combinations and/or integrations of the embodiments described herein.

While the invention has been described in terms of several embodiments, those of skill in the art will recognize that the invention is not limited to the embodiments described, but can be practiced with modification and alteration within the spirit and scope of the appended claims. The description is thus to be regarded as illustrative instead of limiting.

What is claimed is:

1. A method of obtaining cardiac data, comprising:
acquiring vibrational cardiac data from a transducer wherein the transducer measures vibration of a surface of a human's body;
separating an unwanted coronary event from vibrational cardiac data, wherein the effects of the unwanted coronary event on vibrational cardiac data are reduced by the separating;
performing a time-to-frequency transformation on at least a portion of a diastolic interval within a heart cycle of the vibrational cardiac data obtained during the separating to obtain a vibrational frequency power spectrum estimate; and
evaluating the vibrational frequency power spectrum estimate for a condition of coronary artery blood flow turbulence.

2. The method of claim 1, wherein the performing is restricted to at least a first time slot of the diastolic interval.

3. The method of claim 2, further comprising:
averaging vibrational frequency power spectra estimates from an ensemble of heart cycles, whereby a signal-to-noise ratio is increased.

4. The method of claim 3, further comprising:
performing a time-to-frequency transformation on a second time slot of the diastolic interval to obtain a second vibrational frequency power spectrum estimate and the evaluating utilizes the vibrational frequency power spectrum estimate and the second vibrational frequency power spectrum estimate.

5. The method of claim 3, wherein vibrational frequency power spectra estimates corresponding to a given time slot, from a plurality of sensors, are averaged together.

6. The method of claim 4, wherein the evaluating determines whether a shape of a feature changed between the vibrational frequency power spectrum estimate and the second vibrational frequency power spectrum estimate.

7. The method of claim 6, wherein the feature is selected from the group consisting of a low frequency plateau, a roll-off of a low frequency plateau, a spread spectrum energy swath, a frequency band limited whistle, and a high frequency plateau, a roll-off over a band of frequency, and a user defined feature.

8. The method of claim 7, wherein the feature provides information about a physical characteristic of a blockage within a coronary artery.

9. The method of claim 1, wherein the evaluating identifies a feature in the vibrational frequency power spectrum estimate and the feature is selected from the group consisting of a low frequency plateau, a roll off of a low frequency plateau, a spread spectrum energy swath, a frequency band limited whistle, a high frequency plateau, a roll-off over a band of frequency, and a user defined feature.

10. The method of claim 9, wherein the feature provides information about a physical characteristic of a blockage within a coronary artery.

11. The method of claim 4, wherein the at least a portion of the diastolic interval and the second time slot of the diastolic interval do not overlap in time.

12. The method of claim 4, wherein the at least a portion of the diastolic interval and the second time slot of the diastolic, interval partially overlap in time.

13. The method of claim 5, further comprising:
dividing the diastolic interval into a plurality of time slots, wherein the performing is performed on each time slot within the plurality of time slots to produce a vibrational frequency power spectrum estimate for each time slot.

14. A method of obtaining cardiac data, comprising:
acquiring vibrational cardiac data from a transducer wherein the transducer measures vibration of a surface of a human's body;
separating an unwanted coronary event from the vibrational cardiac data, wherein the effects of the unwanted coronary event on the vibrational cardiac data are reduced by the separating;
performing a time-to-frequency transformation on at least a portion of a diastolic interval within a heart cycle of the vibrational cardiac data obtained during the separating, the performing, results in a vibrational frequency power spectrum estimate; and
identifying a feature in the vibrational frequency power spectrum estimate that is associated with an occlusion in a coronary artery, wherein the identifying is accomplished with at least one comparison measurement, the at least one comparison measurement is a separate measurement made from a different human of a vibrational frequency power spectrum estimate from at least a portion of a diastolic interval.

15. The method of claim 14, wherein the feature is associated with a state of health of a coronary artery and the feature is selected from the group consisting of a low frequency plateau, a roll-off of a low frequency plateau, a swath, a whistle, a high frequency plateau, a roll-off over a band of frequency, and a user defined feature.

16. The method of claim 15 wherein the state of health includes a partial blockage of a coronary artery.

17. The method of claim 15, wherein the state of health does not include a partial blockage of a coronary artery.

18. The method of claim 14, wherein, the acquiring utilizes an array of transducers, and the performing creates a vibrational frequency power spectrum estimate for each channel of the array, further comprising:
averaging the vibrational frequency power spectrum estimate for at least two channels of the array, for an ensemble of heart cycles to produce a time averaged vibrational frequency power spectrum estimate for each of the at least two channels; and
averaging together the time averaged vibrational frequency power spectrum estimates for the at least two channels, whereby the signal-to-noise ratio is improved.

19. The method of claim 14, wherein the transducer is selected from the group consisting of a film sensor, a laser, a detector of surface motion.

20. The method of claim 14, wherein the identifying identifies multiple features.

21. The method of claim 14, wherein the second measurement is part of a data base of measurements that have been previously identified with a variety of states of health of coronary arteries.

22. A method of obtaining cardiac data, comprising:
acquiring vibrational cardiac data from a surface of a human's body with a transducer non-invasively, the vibrational cardiac data occurs during at least a portion of a diastolic interval within a heart cycle;
partitioning the at least the portion of the diastolic interval within the heart cycle into at least two time slots;
performing a time-to-frequency transformation on the vibrational cardiac data within each of the at least two time slots, the performing results in at least two vibrational frequency power spectra estimates, and
evaluating the at least two vibrational frequency power spectra estimates to determine if a difference exists over at least one region of the at least two vibrational frequency power spectra estimates.

23. The method of claim 22, wherein the difference is used to assess whether coronary artery blood flow turbulence is indicated by the vibrational cardiac data.

24. The method of claim 23, wherein the difference is used to identify a feature in at least one of the at least two diastolic interval vibrational frequency power spectra that is associated with a state of health of a coronary artery.

25. The method of claim 24, wherein the feature is selected from the group consisting of a low frequency plateau, a roll-off of a low frequency plateau, a spread spectrum swath, a frequency band limited whistle, a high frequency plateau, a roll-off over a band of frequency, and a user defined feature.

26. The method of claim 25 wherein the state of health includes a partial blockage of a coronary artery.

27. The method of claim 25, wherein the state of health does not include a partial blockage of a coronary artery.

28. The method of claim 22, wherein the evaluating further comprises:
using a comparison measurement of vibrational cardiac data obtained from a different human during the evaluating.

29. The method of claim 28, wherein the comparison measurement is used to identify a feature in at least one of the at least two diastolic interval vibrational frequency power spectrum estimates and the feature is selected from the group consisting of a low frequency plateau, a roll-off of a low frequency plateau, a spread spectrum swath, a frequency band limited whistle, a high frequency plateau, a roll-off over a band of frequency, and a user defined feature.

30. An apparatus to Obtain cardiac data, comprising:
a data processing system, the data processing system is configured to process vibrational cardiac data;
a computer readable medium containing executable computer program instructions, which when executed by the data processing system, cause the data processing system to perform a method comprising:
receiving vibrational cardiac data from a transducer wherein the transducer measures vibration of a surface of a human's body;
separating an unwanted coronary event from the vibrational cardiac data;
performing a time-to-frequency transformation on the vibrational cardiac data from at least a portion of a diastolic interval within a heart cycle to obtain a vibrational frequency power spectrum estimate; and
identifying, a feature in the vibrational frequency power spectrum estimate that is associated with a condition of coronary artery blood flow turbulence and a state of health of a coronary artery.

31. The apparatus of claim 30, further comprising:
a transducer, the transducer is configured to measure vibration of a surface of the human's body non-invasively.

32. The apparatus of claim 30, wherein the transducer is selected from the group consisting of a film sensor, a laser, a detector of surface motion, and a user specified sensor.

33. The apparatus of claim 32, wherein the receiving utilizes an array of transducers, and the performing creates a vibrational frequency power spectrum estimate for each channel of the array and then averages the vibrational frequency power spectra estimates together for the heart cycle.

34. The apparatus of claim 30, wherein vibrational frequency power spectra from an ensemble of heart cycles are averaged.

35. The apparatus of claim 30, wherein the method performed by the data processing system further comprising:
performing a time-to-frequency transformation on a second time slot of the diastolic interval to obtain a second vibrational frequency power spectrum estimate and the identifying is done by comparing the vibrational frequency power spectrum estimate and the second vibrational frequency power spectrum estimate.

36. The apparatus of claim 30, wherein the feature is selected from the group consisting of a low frequency plateau, a roll-off of a low frequency plateau, a spread spectrum swath, a frequency band limited whistle, a high frequency plateau, a roll-off over a band of frequency, and a user defined feature.

37. The apparatus of claim 36 wherein the state of health includes a partial blockage of a coronary artery.

38. The apparatus of claim 36, wherein the state of health does not include a partial blockage of a coronary artery.

39. The apparatus of claim 30, wherein the unwanted coronary event is selected from the group consisting of closure within a heart valve, and blood flow through an open heart valve.

40. The apparatus of claim 30, the method performed by the data processing system further comprising;
dividing the diastolic interval into a plurality of time slots, wherein the performing is performed on each time slot within the plurality of time slots to produce vibrational frequency power spectrum estimate for each time slot.

41. The apparatus of claim 40, wherein the receiving utilizes an array of transducers, and the performing creates a vibrational frequency power spectrum estimate for each channel of the array, the method performed by the data processing system further comprising:
averaging the vibrational frequency power spectrum estimate for a particular time slot for an ensemble of heart cycles to produce a time averaged vibrational frequency power spectrum estimate for at least two channels of the array; and
averaging together the time averaged vibrational frequency power spectrum estimates for the at least two channels, whereby a signal-to-noise ratio is improved.

42. A method of obtaining cardiac data, comprising:
acquiring vibrational cardiac data from a transducer wherein the transducer measures vibration of a surface of a human's body;
separating an unwanted coronary event from vibrational cardiac data;
extracting a transient event from the vibrational cardiac data, the transient event occurs during, a diastolic interval within a heart cycle; and
evaluating the transient event for a condition of coronary artery blood flow turbulence.

43. The method of claim 42, the extracting further comprising:
dividing the diastolic interval into at least two time slots; and
performing a time to frequency transformation on the vibrational cardiac data acquired within the at least two time slots to produce at least two vibrational frequency power spectra estimates.

44. The method of claim 43, further comprising;
evaluating the at least vibrational frequency power spectra estimates for a feature that is associated with a condition of health of a coronary artery.

45. A computer-readable storage medium storing program code for causing a data processing system to perform the steps comprising:
receiving vibrational cardiac data from a transducer wherein the transducer measures vibration of a surface of a human's body;
separating an unwanted coronary event from the vibrational cardiac data;
performing a time-to-frequency transformation on the vibrational cardiac data from at least a portion of a diastolic interval within a heart cycle to obtain a vibrational frequency power spectrum estimate; and
identifying a feature in the vibrational frequency power spectrum estimate that is associated with a condition of coronary artery blood flow turbulence and a state of health of a coronary artery.

46. The computer-readable storage medium of claim 45, wherein the receiving utilizes an array of transducers, and the performing creates a vibrational frequency power spectrum estimate for each channel of the array and then averages the vibrational frequency power spectra estimates together for the heart cycle.

47. The computer-readable storage medium of claim 45, wherein vibrational frequency power spectra from an ensemble of heart cycles are averaged.

48. The computer-readable storage medium of claim 45, the steps further comprising:
performing a time-to-frequency transformation on a second time slot of the diastolic interval to obtain a second vibrational frequency power spectrum estimate and the identifying is done by comparing the vibrational frequency power spectrum estimate and the second vibrational frequency power spectrum estimate.

49. The computer-readable storage medium of claim 45, wherein the feature is selected from the group consisting; of a low frequency plateau, a roll-off of a low frequency plateau, a spread spectrum swath, a frequency band limited whistle, a high frequency plateau, a roll-off over a band of frequency, and a user defined feature.

50. The computer-readable storage medium of claim 49 wherein the state of health includes a partial blockage, of a coronary artery.

51. The computer-readable storage medium of claim 49, wherein the state of health does not include a partial blockage of a coronary artery.

52. The computer-readable storage medium of claim 45, wherein the unwanted coronary event is selected from the group consisting of closure within a heart valve, and blood flow through an open heart valve.

53. The computer-readable storage medium of claim 45, the steps further comprising:
dividing the diastolic interval into a plurality of time slots, wherein the performing is performed on each time slot within the plurality of time slots to produce a vibrational frequency power spectrum estimate for each time slot.

54. The computer-readable storage medium of claim 53, wherein the receiving utilizes an array of transducers, and the performing creates a vibrational frequency power spectrum estimate for each channel of the array, the steps further comprising:
averaging the vibrational frequency power spectrum estimate for a particular time slot for an ensemble of heart cycles to produce a time averaged vibrational frequency power spectrum estimate for at least two channels of the array; and
averaging together the time averaged vibrational frequency power spectrum estimates for the at least two channels, whereby a signal-to-noise ratio is improved.

55. A computer-readable storage medium storing program code for causing a data processing system to perform the steps comprising:
acquiring vibrational cardiac data from a transducer wherein the transducer measures vibration of a surface of a human's body;
separating an unwanted coronary event from vibrational earth ac data, wherein the effects of the unwanted coronary event on vibrational cardiac data are reduced by the separating;
performing a time-to-frequency transformation on at least a portion of a diastolic interval within a heart cycle of the vibrational cardiac data obtained during the separating to obtain a vibrational frequency power spectrum estimate; and
evaluating the vibrational frequency power Spectrum estimate for a condition of coronary artery blood flow turbulence.

56. The computer-readable storage medium of claim 55, wherein the performing is restricted to at least a first time slot of the diastolic interval.

57. The computer-readable storage medium of claim 56, the steps further comprising:
averaging vibrational frequency power spectra estimates from an ensemble of heart cycles, whereby a signal-to-noise ratio is increased.

58. The computer-readable storage medium of claim 57, the steps further comprising:
performing a time-to-frequency transformation on a second time slot of the diastolic interval to obtain a second vibrational frequency power spectrum estimate and the evaluating utilizes the vibrational frequency power spectrum estimate and the second vibrational frequency power spectrum estimate.

59. The computer-readable storage medium of claim 57, wherein vibrational frequency power spectra estimates corresponding to a given time slot, from a plurality of sensors, are averaged together.

60. The computer-readable storage medium of claim 58, wherein the evaluating determines whether a shape of a feature changed between the vibrational frequency power spectrum estimate and the second vibrational frequency power spectrum estimate.

61. The computer-readable storage medium of claim 60, wherein the feature is selected from the group consisting of a low frequency plateau, a roll-off of a low frequency plateau, a spread spectrum energy swath, a frequency band limited whistle, and a high frequency plateau, a roll-off over a band of frequency, and a user defined feature.

62. The computer-readable storage medium of claim 61, wherein the feature provides information about a physical characteristic of a blockage within a coronary artery.

63. The computer-readable storage medium of claim 55, wherein the evaluating identifies a feature in the vibrational frequency power spectrum estimate and the feature is selected from the group consisting of a low frequency plateau, a roll-off of a low frequency plateau, a spread spectrum energy swath, a frequency band limited whistle, a high frequency plateau, a roll-off over a band of frequency, and a user defined feature.

64. The computer-readable storage medium of claim 63, wherein the feature provides information about a physical characteristic of a blockage within a coronary artery.

65. The computer-readable storage medium of claim 8, Wherein the at least a portion of the diastolic interval and the second time slot of the diastolic interval do not overlap in tune.

66. The computer-readable storage medium of claim 58, wherein the at least a portion of the diastolic interval and the second time slot of the diastolic interval partially overlap in time.

67. The computer-readable storage medium of claim 59, the steps further comprising:
dividing the diastolic interval into a plurality of time slots, wherein the performing is performed on each time slot within the plurality of time slots to produce a vibrational frequency power spectrum estimate for each time slot.

68. A computer-readable storage medium storing program code for causing a data processing system to perform the steps comprising:
acquiring vibrational cardiac data from a transducer wherein the transducer measures vibration of a surface of a human's body;
separating an unwanted coronary event from the vibrational cardiac data, wherein the effects of the unwanted coronary event on the vibrational cardiac data are reduced by the separating;
performing a time-to-frequency transformation on at least a portion of a diastolic interval within a heart cycle of the vibrational cardiac data obtained during the separating, the performing results in a vibrational frequency power spectrum estimate; and
identifying a feature in the vibrational frequency power spectrum estimate that is associated with an occlusion in a coronary artery, wherein the identifying is accomplished with at least one comparison measurement, the at least one comparison measurement is a separate measurement made from a different human of a vibrational frequency power spectrum estimate from at least a portion of a diastolic interval.

69. The computer-readable storage medium of claim 68, wherein the feature is associated with a state of health of a coronary artery and the feature is selected from the group consisting of a low frequency plateau, a roll-off of a low frequency plateau, a swath, a whistle, a high frequency plateau, a roll-off over a band of frequency, and a user defined feature.

70. The computer-readable storage medium of claim 69 wherein the state of health includes a partial blockage of a coronary artery.

71. The computer-readable storage medium of claim 69, wherein the state of health does not include a partial blockage of a coronary artery.

72. The computer-readable storage medium of claim 68, wherein the acquiring utilizes an array of transducers, and the performing creates a vibrational frequency power spectrum estimate for each channel of the array, the steps further comprising:
averaging the vibrational frequency power spectrum estimate for at least two channels of the array, for an ensemble of heart cycles to produce a time averaged vibrational frequency power spectrum estimate for each of the at least two channels; and
averaging together the time averaged vibrational frequency power spectrum estimates for the at least two channels, whereby the signal-to-noise ratio is improved.

73. The computer-readable storage medium of claim 68, wherein the transducer is selected from the group consisting of a film sensor, a laser, a detector of surface motion.

74. The computer-readable storage medium of claim 68, wherein the identifying identifies multiple features.

75. The computer-readable storage medium of claim 68, wherein the second measurement is part of a data base of measurements that have been previously identified with a variety of states of health of coronary arteries.

76. A computer-readable storage medium storing program code for causing a data processing system to perform the steps comprising:
acquiring vibrational cardiac data from a surface of a human's body with a transducer non-invasively, the vibrational cardiac data occurs during at least a portion of a diastolic interval within a heart cycle;
partitioning the at least the portion of the diastolic interval within the heart into at least two time slots;
performing a time-to-frequency transformation on the vibrational cardiac data within each of the at least two time slots, the performing results in at least to vibrational frequency power spectra estimates; and
evaluating the at least two vibrational frequency power spectra estimates to determine if a difference exists over at least one region of the at least two vibrational frequency power spectra estimates.

77. The computer-readable storage medium of claim 76, wherein the difference is used to assess whether coronary artery blood flow turbulence is indicated by the vibrational cardiac data.

78. The computer-readable storage medium of claim 77, wherein the difference is used to identify a feature in at least one of the at least two diastolic interval vibrational frequency power spectra that is associated with a state of health of a coronary artery.

79. The computer-readable storage medium of claim 78, wherein the feature is selected from the group consisting of a low frequency plateau, a roll-off of a low frequency plateau, a spread spectrum swath, a frequency band limited whistle, a high frequency plateau, a roll-off over a and of frequency, and a user defined feature.

80. The computer-readable storage medium of claim 79 wherein the state of health includes a partial blockage of a coronary artery.

81. The computer-readable storage medium of claim 79, wherein the state of health does not include a partial blockage of a coronary artery.

82. The computer-readable storage medium of claim 76, wherein the evaluating further comprises:
using a comparison measurement of vibrational cardiac data obtained from a different human during the evaluating.

83. The computer-readable storage medium of claim 82, wherein the comparison measurement is used to identify a feature in at least one of the at least two diastolic interval vibrational frequency power spectrum estimates and the feature is selected from the group consisting of a low frequency plateau, a roll-off of a low frequency plateau, a spread spectrum swath, a frequency band limited whistle, a high frequency plateau, a roll-off over a band of frequency, and a user defined feature.

84. A computer-readable storage medium storing program code for causing a data processing system to perform the steps comprising:
acquiring vibrational cardiac data from a transducer wherein the transducer measures vibration of a surface of a human's body;
separating an unwanted coronary event from vibrational cardiac data;
extracting a transient event from the vibrational cardiac data, the transient event occurs during a diastolic interval within a heart cycle, and
evaluating the transient event for a condition of coronary artery blood flow turbulence.

85. The computer-readable storage medium of claim 84, the extracting further comprising:
dividing the diastolic interval into at least two time slots; and
performing a time to frequency transformation on the vibrational cardiac data acquired within the at least two time slots to produce at least two vibrational frequency power spectra estimates.

86. The computer-readable storage medium of claim 85, the steps further comprising;
evaluating the at least vibrational frequency power spectra estimates for a feature that is associated with a condition of health of a coronary artery.

87. A system for execution by a data processing system for obtaining cardiac data, the system comprising:
an interface for receiving vibrational cardiac data, wherein the vibrational cardiac data is acquired from a transducer, the transducer measures vibration of a surface of a human's body;
a processor, the processor is in electrical communication with the interface; and
a computer program for processing the vibrational cardiac data, the computer program and the processor to cause the data processing system to perform the steps comprising:
separating an unwanted coronary event from vibrational cardiac data, wherein the effects of the unwanted coronary event on vibrational cardiac data are reduced by the separating;
performing a time-to-frequency transformation on at least a portion of a diastolic interval within a heart cycle of the vibrational cardiac data obtained during the separating to obtain a vibrational frequency power spectrum estimate; and evaluating the vibrational frequency power spectrum estimate for a condition of coronary artery blood flow turbulence.

88. The system of claim 87, wherein the performing is restricted to at least a first time slot of the diastolic interval.

89. The system of claim 88, the steps further comprising: averaging vibrational frequency power spectra estimates from an ensemble of heart cycles, whereby a signal-to-noise ratio is increased.

90. The system of claim 89, the steps further comprising: performing a time-to-frequency transformation on a second time slot of the diastolic interval to obtain a second vibrational frequency power spectrum estimate and the evaluating utilizes the vibrational frequency power spectrum estimate and the second vibrational frequency power spectrum estimate.

91. The system of claim 89, wherein vibrational frequency power spectra estimates corresponding to a given time slot, from a plurality of sensors, are averaged together.

92. The system of claim 90, wherein the evaluating determines whether a shape of a feature changed between the vibrational frequency.

93. The system of claim 92, wherein the feature is selected from the group consisting of a low frequency plateau, a roll-off of a low frequency plateau, a spread spectrum energy swath, a frequency band limited whistle, and a high frequency plateau, a roll-off over a band of frequency, and a use defined feature.

94. The system of claim 93, wherein the feature provides information about a physical characteristic of a blockage within a coronary artery.

95. The system of claim 87, wherein the evaluating identifies a feature in the vibrational frequency power spectrum estimate and the feature is selected from the group consisting of a low frequency plateau, a roll-off of a low frequency plateau, a spread spectrum energy swath, a frequency band limited whistle, a high frequency plateau, a roll-off over a band of frequency, and a user defined feature.

96. The system of claim 95, wherein the feature provides information about a physical characteristic of a blockage within a coronary artery.

97. The system of claim 90, wherein the at least a portion of the diastolic interval and the second time slot of the diastolic interval do not overlap in time.

98. The system of claim 90, wherein the at least a portion of the diastolic interval and the second time slot of the diastolic interval partially overlap in time.

99. The system of claim 91, the steps further comprising: dividing the diastolic interval into a plurality of time slots, wherein the performing is performed on each time slot within the plurality of time slots to produce a vibrational frequency power spectrum estimate for each time slot.

100. A system for execution by a data processing system for obtaining cardiac data, the system comprising:
an interface for receiving vibrational cardiac data, wherein the vibrational cardiac data is acquired from a transducer, the transduce measures vibration of a surface of a human's body;
a processor, the processor is in electrical communication with the interface; and
a computer program for processing the vibrational cardiac data, the computer program and the processor to cause the data processing system to perform the steps comprising:
separating an unwanted coronary event from the vibrational cardiac data, wherein the effects of the unwanted coronary event on the vibrational cardiac data are reduced by the separating;
performing a time-to-frequency transformation on at least a portion of a diastolic interval within a heart cycle of the vibrational cardiac data obtained during the separating, the performing results in a vibrational frequency power spectrum estimate; and
identifying a feature in the vibrational frequency power spectrum estimate that is associated with an occlusion in a coronary artery, wherein the identifying is accomplished with at least one comparison measurement, the at least one comparison measurement is a separate measurement made from a different human of a vibrational frequency power spectrum estimate from at least a portion of a diastolic interval.

101. The system of claim 100, wherein the feature is associated with a state of health of a coronary artery and the feature is selected from the group consisting of a low frequency plateau, a roll-off of a low frequency plateau, a swath, a whistle, a high frequency plateau, a roll-off over a band of frequency, and a user defined feature.

102. The system of claim 101 wherein the state of health includes a partial blockage of a coronary artery.

103. The system of claim 101, wherein the state of health does not include a partial blockage of a coronary artery.

104. The system of claim 100, wherein the acquiring utilizes an array of transducers, and the performing creates a vibrational frequency power spectrum estimate for each channel of the array, the steps further comprising:
averaging the vibrational frequency power spectrum estimate for at least two channels of the array, for an ensemble of heart cycles to produce a time averaged vibrational frequency power spectrum estimate for each of the at least two channels; and
averaging together the time averaged vibrational frequency power spectrum estimates for the at least two channels, whereby the signal-to-noise ratio is improved.

105. The system of claim 100, wherein the transducer is selected from the group consisting of a film sensor, a laser, a detector of surface motion.

106. The system of claim 100, wherein the identifying identifies multiple features.

107. The system of claim 100, wherein the second measurement is part of a data base of measurements that have been previously identified with a variety of states of health of coronary arteries.

108. A system for execution by a data processing, system for obtaining cardiac data, the system comprising:
an interface for receiving vibrational cardiac data, wherein the vibrational cardiac data is acquired from a transducer, the transducer measures vibration of a surface of a human's body non-invasively;
a processor, the processor is in electrical communication with the interface; and
a computer program for processing the vibrational cardiac data, the computer program and the processor to cause the data processing system to perform the steps comprising:
acquiring vibrational cardiac data during at least a portion of a diastolic interval within a heart cycle;
partitioning the at least the portion of the diastolic interval within the heart cycle into at least two time slots;
performing a time-to-frequency transformation on the vibrational cardiac data within each of the at least two time slots, the performing results in at least two vibrational frequency power spectra estimates; and evaluating the at least two vibrational frequency power spectra estimates to determine if a difference exists over at least one region of the at least two vibrational frequency power spectra estimates.

109. The system of claim 108, wherein the difference is used to assess whether coronary artery blood flow turbulence is indicated by the vibrational cardiac data.

110. The system of claim 109, wherein the difference is used to identify a feature in at least one of the at least two diastolic interval vibrational frequency power spectra that is associated with a state of health of a coronary artery.

111. The system of claim 110, wherein the feature is selected from the group consisting of a low frequency plateau, a roll-off of a low frequency plateau, a spread spectrum swath, a frequency band limited whistle, a high frequency plateau, a roll-off over a band of frequency, and a user defined feature.

112. The system of claim 111 wherein the state of health includes a partial blockage of a coronary artery.

113. The system of claim 111, wherein the state of health does not include a partial blockage of a coronary art.

114. The system of claim 108, wherein the evaluating further comprises:
using a comparison measurement of vibrational cardiac data obtained from a different human during the evaluating.

115. The system of claim 114, wherein the comparison measurement is used to identify a feature in at least one of the at least two diastolic interval vibrational frequency power spectrum estimates and the feature is selected from the group consisting of a low frequency plateau, a roll-off of a low frequency plateau, a spread spectrum swath, a frequency band limited whistle, a high frequency plateau, a roll-off over a band of frequency, and a user defined feature.

116. A system for execution by a data processing system for obtaining cardiac data, the system comprising:
an interface for receiving vibrational cardiac data, wherein the vibrational cardiac data is acquired from a transducer, the transducer measures vibration of a surface of a human's body;
a processor, the processor is in electrical communication with the interface; and
a computer program for processing the vibrational cardiac data, the computer program and the processor to cause the data processing system to perform the steps comprising:
separating an unwanted coronary event from vibrational cardiac data;
extracting a transient event from the vibrational cardiac data, the transient event occurs during a diastolic interval within a heart cycle; and
evaluating the transient event for a condition of coronary artery blood flow turbulence.

117. The system of claim 116, the extracting further comprising:
dividing the diastolic interval into at least two time slots; and
performing a time to frequency transformation on the vibrational cardiac data acquired within the at least two time slots to produce at least two vibrational frequency power spectra estimates.

118. The system of claim 117, the steps further comprising:
evaluating the at least vibrational frequency power spectra estimates for a feature that is associated with a condition of health of a coronary artery.

* * * * *